(12) United States Patent
Gjetting et al.

(10) Patent No.: US 11,807,688 B2
(45) Date of Patent: Nov. 7, 2023

(54) ANTI-AXL ANTIBODIES AND COMPOSITIONS

(71) Applicant: SYMPHOGEN A/S, Ballerup (DK)

(72) Inventors: Torben Gjetting, Jyllinge (DK); Trine Lindsted, Farum (DK); Anton Willer, Virum (DK); Anne Worsaae, Lyngby (DK); Maria Carlsen Melander, Bunkeflostrand (SE); Janus Schou Jakobsen, Gentofte (DK); Randi Westh Hansen, Roskilde (DK)

(73) Assignee: LES LABORATOIRES SERVIER, Suresnes (FR)

( * ) Notice: Subject to any disclaimer, the term of this patent is extended or adjusted under 35 U.S.C. 154(b) by 182 days.

(21) Appl. No.: 17/186,465

(22) Filed: Feb. 26, 2021

(65) Prior Publication Data
US 2021/0269532 A1 Sep. 2, 2021

Related U.S. Application Data

(60) Provisional application No. 62/982,852, filed on Feb. 28, 2020.

(51) Int. Cl.
| | | |
|---|---|---|
| *C07K 16/28* | (2006.01) | |
| *A61P 35/00* | (2006.01) | |
| *A61K 45/06* | (2006.01) | |
| *A61K 39/00* | (2006.01) | |

(52) U.S. Cl.
CPC .......... *C07K 16/2863* (2013.01); *A61K 45/06* (2013.01); *A61P 35/00* (2018.01); *A61K 2039/505* (2013.01)

(58) Field of Classification Search
None
See application file for complete search history.

(56) References Cited

U.S. PATENT DOCUMENTS

| 8,853,369 B2 | 10/2014 | Pei et al. |
| 9,175,091 B2 | 11/2015 | Kitazawa et al. |
| 2017/0349658 A1 | 12/2017 | Micklem et al. |

FOREIGN PATENT DOCUMENTS

| WO | 2017/009258 A1 | 1/2017 | |
| WO | 2017/220695 A1 | 12/2017 | |
| WO | WO-2017220695 A1 * | 12/2017 | ............. A61K 45/06 |
| WO | 2019/197506 A1 | 10/2019 | |

OTHER PUBLICATIONS

Hummer et al. Advances in computational structure-based antibody design. Current Opinion in Structural Biology (2022) 74:102379 (Year: 2022).*
Chailyan et al. The association of heavy and light chain variable domains in antibodies: implications for antigen specificity. FEBS Journal 278 (2011) 2858-2866 (Year: 2011).*

(Continued)

*Primary Examiner* — Joanne Hama
*Assistant Examiner* — Miles Joseph Delahoussaye
(74) *Attorney, Agent, or Firm* — Steptoe & Johnson LLP; Z. Ying Li; Wyan-Ching M. Lee

(57) ABSTRACT

This invention relates to anti-AXL antibodies and methods of using them in treating diseases and conditions related to AXL activity, e.g., cancer.

19 Claims, 10 Drawing Sheets

Specification includes a Sequence Listing.

(56) References Cited

OTHER PUBLICATIONS

Chailyan et al., "The association of heavy and light chain variable domains in antibodies: implications for antigen specificity," FEBS J. (2011) 278(16): 2858-66.

Hummer et al., "Advances in computational structure-based antibody design," Curr Opin Struct Biol. (2022) 74:102379.

Ishimoto et al., "Promotion of the uptake of PS liposomes and apoptotic cells by a product of growth arrest-specific gene, gas6," J Biochem. (2000) 127(3):411-7.

Ye et al., "An anti-Axl monoclonal antibody attenuates xenograft tumor growth and enhances the effect of multiple anticancer therapies," Oncogene (2010) 29(38):5254-64.

* cited by examiner

| ID | YW327.6S2 IgG1-LALA analogue | 10G5 analogue | Gas-6 |
|---|---|---|---|
| 22995 | 1.1 | 1.3 | 0.0 |
| 23203-1 | 1.1 | 1.2 | 0.1 |
| YW327.6S2 IgG1-LALA analogue | 0.0 | 1.6 | -0.2 |
| 10G5 analogue | 1.2 | -0.3 | -0.3 |
| 22883 | 3.9 | -0.3 | -2.7 |
| Control antibody | 1.3 | 1.2 | 0.8 |

Antibodies in solution (columns) / Surface captured antibodies (rows)

FIG. 6

| Protein | 23203-1 | 22995 | 10G5 analogue | YW327.6S2 IgG1-LALA analogue |
|---|---|---|---|---|
| MoAXL ECD HuIg1 | -0.3 | 0.6 | 0.9 | 1.0 |
| MoAXL ECD HuIg2 | 1.0 | -0.1 | -0.3 | 0.9 |
| MoAXL ECD HuFn1 | -0.2 | -0.1 | -0.2 | 0.5 |
| MoAXL ECD HuFn2 | -0.2 | -0.2 | -0.3 | 0.8 |
| HuAXL_ECD | 1.0 | 1.0 | 1.0 | 1.0 |

FIG. 7

ANTI-AXL ANTIBODIES AND COMPOSITIONS

CROSS-REFERENCE TO RELATED APPLICATION

This application claims priority from U.S. Provisional Patent Application 62/982,852, filed Feb. 28, 2020. The disclosure of that priority application is incorporated by reference herein in its entirety.

SEQUENCE LISTING

The instant application contains a Sequence Listing which has been submitted electronically in ASCII format and is hereby incorporated by reference in its entirety. The electronic copy of the Sequence Listing, created on Feb. 26, 2021, is named 022675_US062_SL.txt and is 42,499 bytes in size.

BACKGROUND OF THE INVENTION

AXL, also known as UFO, JTK11, Tyro7, or ARK, is expressed on subsets of myeloid cells including macrophages and dendritic cells and is a member of the TAM (Tyro3-Axl-Mer) family of receptor tyrosine kinases (RTKs). TAM RTKs are phosphatidylserine-sensing receptors involved in uptake of apoptotic cells by phagocytic cells. These kinases are important for maintaining homeostasis of tissues and organs subject to continuous challenge and cellular turnover. The ligand for AXL is Growth Arrest Specific 6 (GAS6), which functions as a linker between phosphatidylserine on apoptotic cells and AXL and facilitates uptake of cellular debris in a process known as efferocytosis.

Aberrantly elevated TAM activity is strongly associated with tumor progression, epithelial-to-mesenchymal transition, metastasis, and resistance to targeted therapies. AXL-mediated efferocytosis has been shown to enter AXL-expressing cells into an immune-suppressive state with decreased ability to present antigens to T cells and to produce pro-inflammatory cytokines. Upon GAS6-induced activation, AXL provides a strong survival signal to tumor cells through the PI3K/AKT signaling pathway. Elevated expression of GAS6 and AXL is correlated with poor prognosis in cancer patients.

In view of the critical role of AXL in cancer progression, there is a need for new and improved anti-cancer therapies that target AXL.

SUMMARY OF THE INVENTION

The present invention is directed to novel recombinant antibodies targeting AXL, as well as pharmaceutical compositions comprising one or more of these antibodies, and use of the antibodies and pharmaceutical compositions for treatment of cancer. The antibodies and compositions described herein may be used in a method for treating cancer in a patient; may be used for the manufacture of a medicament for treating cancer in a patient; or may be for use in treating cancer in a patient. Compared to currently available treatments for such cancers, including antibody treatments, it is contemplated that the antibodies and compositions described herein may provide a superior clinical response either alone or in combination with another cancer therapeutic.

In some embodiments, the present disclosure provides an anti-AXL antibody or an antigen-binding portion thereof that competes or cross-competes for binding with or binds to the same epitope of human AXL as antibody 23203_1, 23203_2, 23203_3, 23203_4, 22995, or 22883. In certain embodiments, the anti-AXL antibody or antigen-binding portion is defined by the amino acid sequences of the six CDRs, heavy and light chain variable domains, or heavy and light chains of said antibody.

In some embodiments, the present disclosure provides an anti-AXL antibody or an antigen-binding portion thereof, wherein
  a) the heavy chain of said antibody comprises:
     i) heavy chain complementarity determining regions (H-CDR)-1-3 comprising the amino acid sequences of SEQ ID NOs: 5-7, respectively;
     ii) a heavy chain variable domain (VH) comprising an amino acid sequence at least 90% identical to the amino acid sequence of SEQ ID NO: 3;
     iii) a VH comprising the amino acid sequence of SEQ ID NO: 3; or
     iv) a heavy chain (HC) comprising the amino acid sequences of SEQ ID NOs: 3 and 61; and
  b) the light chain of said antibody comprises:
     i) light chain complementarity determining regions (L-CDR)-1-3 comprising the amino acid sequences of SEQ ID NOs: 8-10, respectively;
     ii) a light chain variable domain (VL) comprising an amino acid sequence at least 90% identical to the amino acid sequence of SEQ ID NO: 4;
     iii) a VL comprising the amino acid sequence of SEQ ID NO: 4; or
     iv) a light chain (LC) comprising the amino acid sequences of SEQ ID NOs: 4 and 62.

In some embodiments, the present disclosure provides an anti-AXL antibody or an antigen-binding portion thereof, wherein
  a) the heavy chain of said antibody comprises:
     i) H-CDR-1-3 comprising the amino acid sequences of SEQ ID NOs: 15-17, respectively;
     ii) a VH comprising an amino acid sequence at least 90% identical to the amino acid sequence of SEQ ID NO: 13;
     iii) a VH comprising the amino acid sequence of SEQ ID NO: 13; or
     iv) an HC comprising the amino acid sequences of SEQ ID NOs: 13 and 61; and
  b) the light chain of said antibody comprises:
     i) L-CDR-1-3 comprising the amino acid sequences of SEQ ID NOs: 18-20, respectively;
     ii) a VL comprising an amino acid sequence at least 90% identical to the amino acid sequence of SEQ ID NO: 14;
     iii) a VL comprising the amino acid sequence of SEQ ID NO: 14; or
     iv) an LC comprising the amino acid sequences of SEQ ID NOs: 14 and 62.

In some embodiments, the present disclosure provides an anti-AXL antibody or an antigen-binding portion thereof, wherein
  a) the heavy chain of said antibody comprises:
     i) H-CDR-1-3 comprising the amino acid sequences of SEQ ID NOs: 25-27, respectively;
     ii) a VH comprising an amino acid sequence at least 90% identical to the amino acid sequence of SEQ ID NO: 23;

iii) a VH comprising the amino acid sequence of SEQ ID NO: 23; or
iv) an HC comprising the amino acid sequences of SEQ ID NOs: 23 and 61; and
b) the light chain of said antibody comprises:
i) L-CDR-1-3 comprising the amino acid sequences of SEQ ID NOs: 28-30, respectively;
ii) a VL comprising an amino acid sequence at least 90% identical to the amino acid sequence of SEQ ID NO: 24;
iii) a VL comprising the amino acid sequence of SEQ ID NO: 24; or
iv) an LC comprising the amino acid sequences of SEQ ID NOs: 24 and 62.

In some embodiments, the present disclosure provides an anti-AXL antibody or an antigen-binding portion thereof, wherein
a) the heavy chain of said antibody comprises:
i) H-CDR-1-3 comprising the amino acid sequences of SEQ ID NOs: 35-37, respectively;
ii) a VH comprising an amino acid sequence at least 90% identical to the amino acid sequence of SEQ ID NO: 33;
iii) a VH comprising the amino acid sequence of SEQ ID NO: 33; or
iv) an HC comprising the amino acid sequences of SEQ ID NOs: 33 and 61; and
b) the light chain of said antibody comprises:
i) L-CDR-1-3 comprising the amino acid sequences of SEQ ID NOs: 38-40, respectively;
ii) a VL comprising an amino acid sequence at least 90% identical to the amino acid sequence of SEQ ID NO: 34;
iii) a VL comprising the amino acid sequence of SEQ ID NO: 34; or
iv) an LC comprising the amino acid sequences of SEQ ID NOs: 34 and 62.

In some embodiments, the present disclosure provides an anti-AXL antibody or an antigen-binding portion thereof, wherein
a) the heavy chain of said antibody comprises:
i) H-CDR-1-3 comprising the amino acid sequences of SEQ ID NOs: 45-47, respectively;
ii) a VH comprising an amino acid sequence at least 90% identical to the amino acid sequence of SEQ ID NO: 43;
iii) a VH comprising the amino acid sequence of SEQ ID NO: 43; or
iv) an HC comprising the amino acid sequences of SEQ ID NOs: 43 and 61; and
b) the light chain of said antibody comprises:
i) L-CDR-1-3 comprising the amino acid sequences of SEQ ID NOs: 48-50, respectively;
ii) a VL comprising an amino acid sequence at least 90% identical to the amino acid sequence of SEQ ID NO: 44;
iii) a VL comprising the amino acid sequence of SEQ ID NO: 44; or
iv) an LC comprising the amino acid sequences of SEQ ID NOs: 44 and 62.

In some embodiments, the present disclosure provides an anti-AXL antibody or an antigen-binding portion thereof, wherein
a) the heavy chain of said antibody comprises:
i) H-CDR-1-3 comprising the amino acid sequences of SEQ ID NOs: 55-57, respectively;
ii) a VH comprising an amino acid sequence at least 90% identical to the amino acid sequence of SEQ ID NO: 53;
iii) a VH comprising the amino acid sequence of SEQ ID NO: 53; or
iv) an HC comprising the amino acid sequences of SEQ ID NOs: 53 and 61; and
b) the light chain of said antibody comprises:
i) L-CDR-1-3 comprising the amino acid sequences of SEQ ID NOs: 58-60, respectively;
ii) a VL comprising an amino acid sequence at least 90% identical to the amino acid sequence of SEQ ID NO: 54;
iii) a VL comprising the amino acid sequence of SEQ ID NO: 54; or
iv) an LC comprising the amino acid sequences of SEQ ID NOs: 54 and 62.

The present disclosure also provides isolated nucleic acid molecules, vectors, and host cells comprising nucleotide sequences that encode the heavy chain or an antigen-binding portion thereof, the light chain or an antigen-binding portion thereof, or both, of an anti-AXL antibody or antigen-binding portion described herein. Further, the present disclosure provides methods for producing an anti-AXL antibody or antigen-binding portion described herein by culturing said host cells, as well as methods for producing an antibody composition by admixing antibodies or antigen-binding portions described herein.

Other features, objectives, and advantages of the invention are apparent in the detailed description that follows. It should be understood, however, that the detailed description, while indicating embodiments and aspects of the invention, is given by way of illustration only, not limitation. Various changes and modifications within the scope of the invention will become apparent to those skilled in the art from the detailed description.

BRIEF DESCRIPTION OF THE DRAWINGS

FIG. 6 is a table depicting cross-competition results for the indicated antibodies and the AXL ligand, GAS6, tested in a classical sandwich assay by SPR. Data were normalized to correct for differences in recombinant AXL-ECD binding capacities for each antibody on the surface. Sandwiching antibodies are shown as white and blocking antibodies are shown as grey.

FIG. 7 is a table depicting Bio-Layer Interferometry (BLI) responses (nm) for binding of the indicated antibodies to captured human/mouse chimeric proteins, normalized to antibody binding to full-length human AXL-ECD for each antibody. The mouse AXL sequence ("MoAXL") was exchanged for human AXL sequence for domain Ig1, Ig2, Fn1, or Fn2 ("HuIg1," "HuIg2," "HuFn1," and "HuFn2," marked in bold). Grey color represents no binding response; negative responses are due to a slight dissociation of captured antigen from the Penta-His surface. Data are from one representative experiment.

DETAILED DESCRIPTION OF THE INVENTION

Figure 1A:
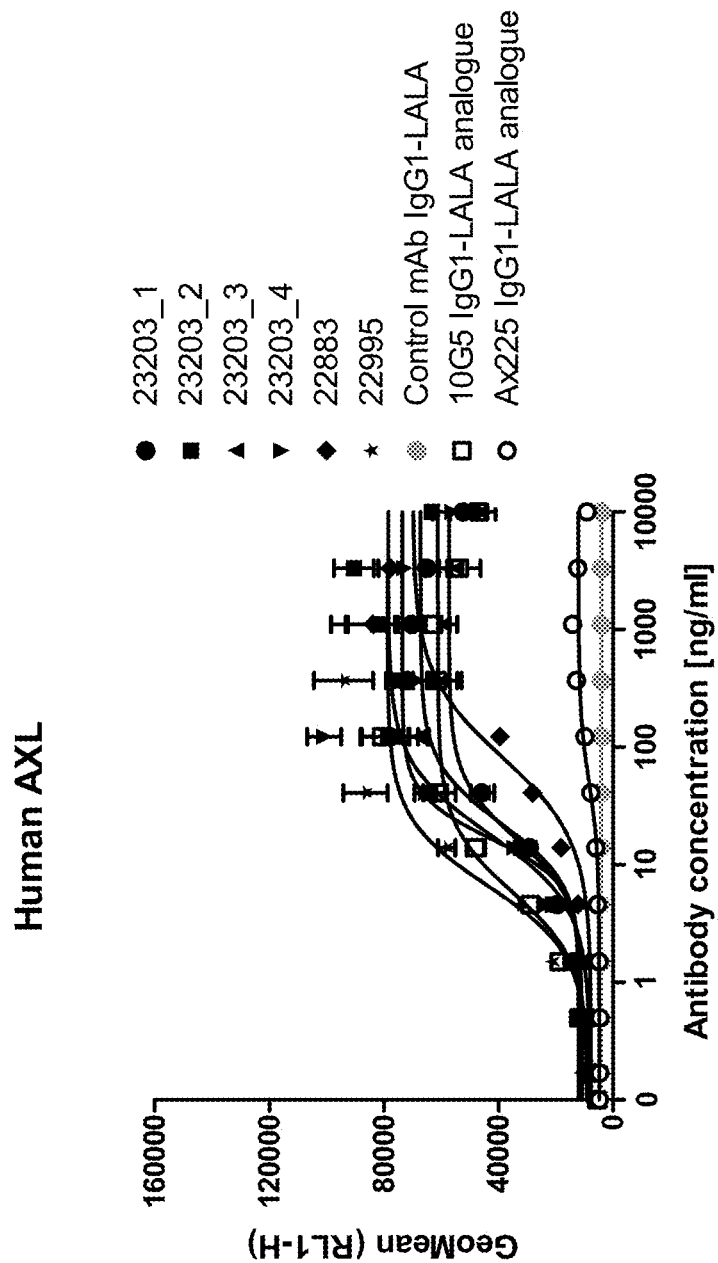
FIGS. 1A-1C are a set of graphs showing the binding profiles of the indicated anti-human AXL antibodies to human (FIG. 1A) and cynomolgus (FIG. 1B) AXL extracellular domain (ECD) transiently expressed on CHO-S cells. Mock transfected CHO-S cells were used as a negative control (FIG. 1C). Data are presented as mean±SEM (n=3).

The present disclosure provides new anti-human AXL antibodies that can be used to inhibit AXL activity in a patient, such as a cancer patient. Unless otherwise stated, as used herein, "AXL" refers to human AXL. A human AXL polypeptide sequence is available under UniProt Accession No. P30530 (UFO_HUMAN) (SEQ ID NO: 63), as shown below:

```
            10         20         30         40         50
    MAWRCPRMGR VPLAWCLALC GWACMAPRGT QAEESPFVGN PGNITGARGL
            60         70         80         90        100
    TGTLRCQLQV QGEPPEVHWL RDGQILELAD STQTQVPLGE DEQDDWIVVS
           110        120        130        140        150
    QLRITSLQLS DTGQYQCLVF LGHQTFVSQP GYVGLEGLPY FLEEPEDRTV
           160        170        180        190        200
    AANTPFNLSC QAQGPPEPVD LLWLQDAVPL ATAPGHGPQR SLHVPGLNKT
           210        220        230        240        250
    SSFSCEAHNA KGVTTSRTAT ITVLPQQPRN LHLVSRQPTE LEVAWTPGLS
           260        270        280        290        300
    GIYPLTHCTL QAVLSDDGMG IQAGEPDPPE EPLTSQASVP PHQLRLGSLH
           310        320        330        340        350
    PHTPYHIRVA CTSSQGPSSW THWLPVETPE GVPLGPPENI SATRNGSQAF
           360        370        380        390        400
    VHWQEPRAPL QGTLLGYRLA YQGQDTPEVL MDIGLRQEVT LELQGDGSVS
           410        420        430        440        450
    NLTVCVAAYT AAGDGPWSLP VPLEAWRPGQ AQPVHQLVKE PSTPAFSWPW
           460        470        480        490        500
    WYVLLGAVVA AACVLILALF LVHRRKKETR YGEVFEPTVE RGELVVRYRV
           510        520        530        540        550
    RKSYSRRTTE ATLNSLGISE ELKEKLRDVM VDRHKVALGK TLGEGEFGAV
           560        570        580        590        600
    MEGQLNQDDS ILKVAVKTMK IAICTRSELE DELSEAVCMK EFDHPNVMRL
           610        620        630        640        650
    IGVCFQGSER ESFPAPVVIL PFMKHGDLHS FLLYSRLGDQ PVYLPTQMLV
           660        670        680        690        700
    KFMADIASGM EYLSTKRFIH RDLAARNCML NENMSVCVAD FGLSKKIYNG
           710        720        730        740        750
    DYYRQGRIAK MPVKWIAIES LADRVYTSKS DVWSFGVTMW EIATRGQTPY
           760        770        780        790        800
    PGVENSEIYD YLRQGNRLKQ PADCLDGLYA LMSRCWELNP QDRPSFTELR
           810        820        830        840        850
    EDLENTLKAL PPAQEPDEIL YVNMDEGGGY PEPPGAAGGA DPPTQPDPKD
           860        870        880        890
    SCSCLTAAEV HPAGRYVLCP STTPSPAQPA DRGSPAAPGQ EDGA
```

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers, and of FR and CDR regions, in the heavy or light chain may be in accordance with IMGT® definitions (Eu numbering; Lefranc et al., *Dev Comp Immunol* 27(1):55-77 (2003)); or the definitions of Kabat, *Sequences of Proteins of Immunological Interest* (National Institutes of Health, Bethesda, Md. (1987 and 1991)); Chothia & Lesk, *J. Mol. Biol.* 196:901-917 (1987); Chothia et al., *Nature* 342:878-883 (1989); MacCallum et al., *J. Mol. Biol.* 262:732-745 (1996); or Honegger and Plückthun, J. Mol. Biol. 309(3): 657-70 (2001).

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein," "isolated polypeptide" or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, e.g., ≤1 µM, ≤100 nM, or ≤10 nM. A $K_D$ binding affinity constant can be measured, e.g., by surface plasmon resonance (e.g., BIAcore™) using the *IBIS* MX96 SPR system from *IBIS* Technologies or the Carterra LSA SPR platform, or by Bio-Layer Interferometry, for example using the Octet™ system from ForteBio.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a minidomain containing the relevant amino acid residues of the conformational epitope. An antibody to a particular epitope can also be generated, e.g., by immunizing an animal with the target molecule of interest (e.g., AXL) or a relevant portion thereof, then screening for binding to the epitope.

One can determine whether an antibody binds to the same epitope as or competes for binding with an anti-AXL antibody of the present disclosure by using methods known in the art, including, without limitation, competition assays, epitope binning, and alanine scanning. In some embodiments, one allows the anti-AXL antibody of the present disclosure to bind to AXL under saturating conditions, and then measures the ability of the test antibody to bind to AXL. If the test antibody is able to bind to AXL at the same time as the reference anti-AXL antibody, then the test antibody binds to a different epitope than the reference anti-AXL antibody. However, if the test antibody is not able to bind to AXL at the same time, then the test antibody binds to the same epitope, an overlapping epitope, or an epitope that is in close proximity to the epitope bound by the anti-AXL antibody of the present disclosure. This experiment can be performed using, e.g., ELISA, RIA, BIACORE™ SPR, Bio-Layer Interferometry or flow cytometry. To test whether an anti-AXL antibody cross-competes with another anti-AXL antibody, one may use the competition method described above in two directions, i.e., determining if the known antibody blocks the test antibody and vice versa. Such cross-competition experiments may be performed, e.g., using an IBIS MX96 or Carterra LSA SPR instrument or the Octet™ system.

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human AXL, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains;

(iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the present disclosure are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesin molecules can be obtained using standard recombinant DNA techniques, e.g., as described herein.

The class (isotype) and subclass of anti-AXL antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant region of the heavy and/or light chains of the antibodies, comparing their amino acid sequences to the known amino acid sequences of various classes and subclasses of immunoglobulins, and determining the class and subclass of the antibodies.

Unless otherwise indicated, all antibody amino acid residue numbers referred to in this disclosure are those under the IMGT® numbering scheme (EU numbering).

Anti-AXL Antibodies

The present disclosure provides antibodies directed against AXL, and antigen-binding portions thereof. In a particular aspect, the antibodies disclosed herein are human antibodies generated from transgenic animals (e.g., rats) that are able to produce antibodies encoded by rearranged human antibody genes. In certain embodiments, the human antibodies may contain certain mutations, e.g., to change primer-derived mutations back to the germline sequence (see, e.g., the "Symplex-corrected" variant sequences in Table 1).

In some embodiments, the anti-AXL antibodies of the present disclosure have the "LALA" mutations (L234A/L235A) in the Fc region. These mutations hinder the antibodies' binding to human FcγR (Fc gamma receptors). Such antibodies are advantageous because they have a low level of secondary effector functions and hence do not deplete effector T cells or target other non-malignant cells.

In some embodiments, the anti-AXL antibody or antigen-binding portion competes or cross-competes for binding to human AXL with, or binds to the same epitope of human AXL as, an antibody comprising:

a) a heavy chain (HC) comprising the amino acid sequences of SEQ ID NOs: 3 and 61 and a light chain (LC) comprising the amino acid sequences of SEQ ID NOs: 4 and 62;

b) an HC comprising the amino acid sequences of SEQ ID NOs: 13 and 61 and an LC comprising the amino acid sequences of SEQ ID NOs: 14 and 62;

c) an HC comprising the amino acid sequences of SEQ ID NOs: 23 and 61 and an LC comprising the amino acid sequences of SEQ ID NOs: 24 and 62;

d) an HC comprising the amino acid sequences of SEQ ID NOs: 33 and 61 and an LC comprising the amino acid sequences of SEQ ID NOs: 34 and 62;

e) an HC comprising the amino acid sequences of SEQ ID NOs: 43 and 61 and an LC comprising the amino acid sequences of SEQ ID NOs: 44 and 62; or f) an HC comprising the amino acid sequences of SEQ ID NOs: 53 and 61 and an LC comprising the amino acid sequences of SEQ ID NOs: 54 and 62.

In some embodiments, the anti-AXL antibody or antigen-binding portion has a heavy chain CDR3 (H-CDR3) amino acid sequence of SEQ ID NO: 7, 17, 27, 37, 47, or 57.

In some embodiments, the anti-AXL antibody or antigen-binding portion has heavy chain CDR1-3 (H-CDR1-3) comprising the amino acid sequences of SEQ ID NOs: 5-7, 15-17, 25-27, 35-37, 45-47, or 55-57, respectively.

In some embodiments, the anti-AXL antibody or antigen-binding portion has a heavy chain variable domain (VH) amino acid sequence that is at least 80%, 85%, 90%, 91%, 92%, 93%, 94%, 95%, 96%, 97%, 98%, or 99% identical to the amino acid sequence of SEQ ID NO: 3, 13, 23, 33, 43, or 53.

In some embodiments, the anti-AXL antibody or antigen-binding portion has a VH comprising the amino acid sequence of SEQ ID NO: 3, 13, 23, 33, 43, or 53.

In some embodiments, the anti-AXL antibody has a VH amino acid sequence that is at least 80%, 85%, 90%, 91%, 92%, 93%, 94%, 95%, 96%, 97%, 98%, or 99% identical to the amino acid sequence of SEQ ID NO: 3, 13, 23, 33, 43, or 53; and a heavy chain constant region amino acid sequence that is at least 80%, 85%, 90%, 91%, 92%, 93%, 94%, 95%, 96%, 97%, 98%, or 99% identical to the amino acid sequence of SEQ ID NO: 61.

In some embodiments, the anti-AXL antibody comprises a VH amino acid sequence of SEQ ID NO: 3, 13, 23, 33, 43, or 53 and a heavy chain constant region amino acid sequence of SEQ ID NO: 61.

In some embodiments, the anti-AXL antibody or antigen-binding portion has a light chain CDR3 (L-CDR3) amino acid sequence of SEQ ID NO: 10, 20, 30, 40, 50, or 60.

In some embodiments, the anti-AXL antibody or antigen-binding portion has light chain CDR1-3 (L-CDR1-3) comprising the amino acid sequences of SEQ ID NOs: 8-10, 18-20, 28-30, 38-40, 48-50, or 58-60, respectively.

In some embodiments, the anti-AXL antibody or antigen-binding portion has a light chain variable domain (VL) amino acid sequence that is at least 80%, 85%, 90%, 91%, 92%, 93%, 94%, 95%, 96%, 97%, 98%, or 99% identical to the amino acid sequence of SEQ ID NO: 4, 14, 24, 34, 44, or 54.

In some embodiments, the anti-AXL antibody or antigen-binding portion has a VL comprising the amino acid sequence of SEQ ID NO: 4, 14, 24, 34, 44, or 54.

In some embodiments, the anti-AXL antibody has a VL amino acid sequence that is at least 80%, 85%, 90%, 91%, 92%, 93%, 94%, 95%, 96%, 97%, 98%, or 99% identical to the amino acid sequence of SEQ ID NO: 4, 14, 24, 34, 44, or 54; and a light chain constant region amino acid sequence that is at least 80%, 85%, 90%, 91%, 92%, 93%, 94%, 95%, 96%, 97%, 98%, or 99% identical to the amino acid sequence of SEQ ID NO: 62.

In some embodiments, the anti-AXL antibody comprises a VL amino acid sequence of SEQ ID NO: 4, 14, 24, 34, 44, or 54 and a light chain constant region amino acid sequence of SEQ ID NO: 62.

In certain embodiments, the anti-AXL antibody comprises any one of the above-described heavy chains and any one of the above-described light chains.

In some embodiments, the anti-AXL antibody or antigen-binding portion of the present disclosure comprises the H-CDR1-3 and L-CDR1-3 amino acid sequences of:
 a) SEQ ID NOs: 5-10, respectively;
 b) SEQ ID NOs: 15-20, respectively;
 c) SEQ ID NOs: 25-30, respectively;
 d) SEQ ID NOs: 35-40, respectively;
 e) SEQ ID NOs: 45-50, respectively; or
 f) SEQ ID NOs: 55-60, respectively.

In some embodiments, the anti-AXL antibody or antigen-binding portion of the present disclosure comprises a VH and a VL that are 80%, 85%, 90%, 91%, 92%, 93%, 94%, 95%, 96%, 97%, 98%, or 99% identical (e.g., 90% identical) to the amino acid sequences of:
 a) SEQ ID NOs: 3 and 4, respectively;
 b) SEQ ID NOs: 13 and 14, respectively;
 c) SEQ ID NOs: 23 and 24, respectively;
 d) SEQ ID NOs: 33 and 34, respectively;
 e) SEQ ID NOs: 43 and 44, respectively; or
 f) SEQ ID NOs: 53 and 54, respectively.

In some embodiments, the anti-AXL antibody or antigen-binding portion of the present disclosure comprises a VH and a VL that comprise the amino acid sequences of:
 a) SEQ ID NOs: 3 and 4, respectively;
 b) SEQ ID NOs: 13 and 14, respectively;
 c) SEQ ID NOs: 23 and 24, respectively;
 d) SEQ ID NOs: 33 and 34, respectively;
 e) SEQ ID NOs: 43 and 44, respectively; or
 f) SEQ ID NOs: 53 and 54, respectively.

In some embodiments, the anti-AXL antibody of the present disclosure comprises:
 a) an HC comprising the amino acid sequences of SEQ ID NOs: 3 and 61 and an LC comprising the amino acid sequences of SEQ ID NOs: 4 and 62;
 b) an HC comprising the amino acid sequences of SEQ ID NOs: 13 and 61 and an LC comprising the amino acid sequences of SEQ ID NOs: 14 and 62;
 c) an HC comprising the amino acid sequences of SEQ ID NOs: 23 and 61 and an LC comprising the amino acid sequences of SEQ ID NOs: 24 and 62;
 d) an HC comprising the amino acid sequences of SEQ ID NOs: 33 and 61 and an LC comprising the amino acid sequences of SEQ ID NOs: 34 and 62;
 e) an HC comprising the amino acid sequences of SEQ ID NOs: 43 and 61 and an LC comprising the amino acid sequences of SEQ ID NOs: 44 and 62; or
 f) an HC comprising the amino acid sequences of SEQ ID NOs: 53 and 61 and an LC comprising the amino acid sequences of SEQ ID NOs: 54 and 62.

The present disclosure also provides an anti-AXL antibody or an antigen-binding portion thereof that competes or cross-competes for binding with, or binds to the same epitope as, antibody 23203_1, 23203_2, 23203_3, 23203_4, 22995, or 22883.

In some embodiments, the anti-AXL antibody or antigen-binding portion of the present disclosure comprises the H-CDR1-3 and L-CDR1-3 amino acid sequences of antibody 23203_1, 23203_2, 23203_3, 23203_4, 22995, or 22883.

In some embodiments, the anti-AXL antibody or antigen-binding portion of the present disclosure comprises a VH and a VL that are at least 80%, 85%, 90%, 91%, 92%, 93%, 94%, 95%, 96%, 97%, 98%, or 99% identical in amino acid sequence to the VH and VL, respectively, of antibody 23203_1, 23203_2, 23203_3, 23203_4, 22995, or 22883.

In some embodiments, the anti-AXL antibody or antigen-binding portion of the present disclosure comprises a VH and a VL that are the VH and VL, respectively, of antibody 23203_1, 23203_2, 23203_3, 23203_4, 22995, or 22883.

In some embodiments, the anti-AXL antibody of the present disclosure is antibody 23203_1, 23203_2, 23203_3, 23203_4, 22995, or 22883, or an antibody with the same amino acid sequences as said antibody.

In any of the embodiments described herein referring to a sequence comprising the H-CDR3 of antibody 23203_1, 23203_2, 23203_3, or 23203_4, said H-CDR3 may be replaced by a variant H-CDR3 where the serine (S) residue in position 2 in sequence CSSREYSSRWHFDYW (SEQ ID NO: 7) is replaced by an alanine (A), so that the H-CDR3 sequence is CASREYSSRWHFDYW (SEQ ID NO: 65). The variant residue is shown in bold/underlined.

In any of the embodiments described herein referring to a sequence comprising the H-FR3 of antibody 23203_1, 23203_2, 23203_3, or 23203_4, said H-FR3 may be replaced by a variant H-FR3 where the aspartate (D) residue in position 32 in sequence NYNPSLKSRVTISVDTSKNQFSLKLSSVTAADTAVYY (SEQ ID NO: 66) is replaced by a glycine (G) residue, so that the H-FR3 sequence is NYNPSLKSRVTISVDTSKNQFSLKLSSVTAAGTAVYY (SEQ ID NO: 67). The variant residue is shown in bold/underlined.

In any of the embodiments described herein referring to the VL of 22995 (SEQ ID NO: 44), said sequence may be replaced by any human IGKV/IGKJ germline sequence. In certain embodiments, the replacement sequence may have L-CDR1, L-CDR2 and L-CDR3 of SEQ ID NOs: 48, 49, and 50, respectively, that are grafted into any human IGKV/IGKJ sequence, thereby replacing the original germline sequence.

The class of an anti-AXL antibody obtained by the methods described herein may be changed or switched with another class or subclass. In some embodiments of the present disclosure, a nucleic acid molecule encoding VL or VH is isolated using methods well known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH sequence, as described above. For example, an anti-AXL antibody that was originally IgM may be class switched to IgG. Further, the class switching may be used to convert one IgG subclass to another, e.g., from IgG$_1$ to IgG$_2$. A κ light chain constant region can be changed, e.g., to a λ light chain constant region, or vice-versa. An exemplary method for producing an antibody of the present disclosure with a desired Ig isotype comprises the steps of isolating a nucleic acid molecule encoding the heavy chain of an anti-AXL antibody and a nucleic acid molecule encoding the light chain of an anti-AXL antibody, obtaining the variable domain of the heavy chain, ligating a coding sequence for the variable domain of the heavy chain with a coding sequence for the constant region of a heavy chain of the desired isotype, expressing the light chain and the heavy chain encoded by the ligated sequence in a cell, and collecting the anti-AXL antibody with the desired isotype.

The anti-AXL antibody of the present disclosure can be an IgG, an IgM, an IgE, an IgA, or an IgD molecule, but is typically of the IgG isotype, e.g., of IgG subclass $IgG_1$, $IgG_{2a}$ or $IgG_{2b}$, $IgG_3$ or $IgG_4$. In some embodiments, the antibody is of the isotype subclass $IgG_1$.

In some embodiments, the anti-AXL antibody may comprise at least one mutation in the Fc region. A number of different Fc mutations are known, where these mutations alter the antibody's effector function. For example, in some embodiments, the anti-AXL antibody comprises at least one mutation in the Fc region that reduces effector function, e.g., mutations at one or more of positions 228, 233, 234 and 235, where amino acid positions are numbered according to the IMGT® numbering scheme.

In some embodiments, e.g., where the antibody is of the $IgG_1$ subclass, one or both of the amino acid residues at positions 234 and 235 may be mutated, for example from Leu to Ala (L234A/L235A). These mutations reduce effector function of the Fc region of $IgG_1$ antibodies. The amino acid positions are numbered according to the IMGT® numbering scheme.

In some embodiments, e.g., where the antibody is of the $IgG_4$ subclass, it may comprise the mutation S228P, where the amino acid position is numbered according to the IMGT® numbering scheme. This mutation is known to reduce undesired Fab arm exchange.

In some embodiments, the anti-AXL antibody or antigen-binding portion binds to human AXL with a $K_D$ of about $5\times10^{-8}$, $4\times10^{-8}$, $3\times10^{-8}$, $2\times10^{-8}$, $1\times10^{-8}$, $9\times10^{-9}$, $8\times10^{-9}$, $7\times10^{-9}$, $6\times10^{-9}$, $5\times10^{-9}$, $4\times10^{-9}$, $3\times10^{-9}$, $2\times10^{-9}$, $1\times10^{-9}$, $9\times10^{-10}$, $8\times10^{-10}$, $7\times10^{-16}$, $6\times10^{-10}$, or $5\times10^{-10}$ M or less.

In some embodiments, the anti-AXL antibody or antigen-binding portion binds to cynomolgus AXL with a $K_D$ of about $9\times10^{-8}$, $8\times10^{-8}$, $7\times10^{-8}$, $6\times10^{-8}$, $5\times10^{-8}$, $4\times10^{-8}$, $3\times10^{-8}$, $2\times10^{-8}$, $1\times10^{-8}$, $9\times10^{-9}$, $8\times10^{-9}$, $7\times10^{-9}$, $6\times10^{-9}$, or $5\times10^{-9}$ or less.

In some embodiments, the anti-AXL antibody or antigen-binding portion inhibits proliferation of H1299 cells in vitro at a concentration of about 1, 5, 10, 15, 20, or 25 µg/mL or less in the presence of GAS6 (e.g., wherein the GAS6 is at a concentration of about 1 µg/mL).

In some embodiments, the anti-AXL antibody or antigen-binding portion does not exhibit agonistic activity, e.g., at a concentration of up to about 1, 5, 10, 15, 20, or 25 µg/mL, in the absence of GAS6.

In some embodiments, the anti-AXL antibody or antigen-binding portion inhibits GAS6-induced uptake of phosphatidylserine-containing liposomes, e.g., at a concentration of about 0.005, 0.01, 0.05, 0.1, 0.5, 1, 2, 4, or 6 µg/mL or less, in MDA-MB-468-AXL cells stably expressing exogenous AXL.

In some embodiments, the anti-AXL antibody or antigen-binding portion inhibits tumor growth in vivo, e.g., at a concentration of about 10 mg/kg or 50 mg/kg.

In some embodiments, the anti-AXL antibody or antigen-binding portion inhibits binding of GAS6 to human AXL.

In some embodiments, the anti-AXL antibody or antigen-binding portion recognizes a different epitope of human AXL than 10G5 and/or YW327.6S2.

In some embodiments, the anti-AXL antibody or antigen-binding portion does not bind to mouse AXL.

In some embodiments, the anti-AXL antibody or antigen-binding portion binds to the Ig1 domain of human AXL. In some embodiments, the anti-AXL antibody or antigen-binding portion binds to the Ig2 domain of human AXL.

The present disclosure also contemplates an anti-AXL antibody or antigen-binding portion described herein with any combination of the above properties.

In some embodiments, an anti-AXL antibody or antigen-binding portion described herein has at least one (e.g., 1, 2, 3, 4, 5, 6, 7, 8, or all 9) of the following properties:
 a) binds to human AXL with a $K_D$ of $3\times10^{-8}$ M or less;
 b) binds to cynomolgus AXL with a $K_D$ of $8\times10^{-8}$ M or less;
 c) does not bind to mouse AXL;
 d) binds to the Ig1 or Ig2 domain of human AXL;
 e) inhibits binding of GAS6 to human AXL;
 f) inhibits proliferation of H1299 cells in vitro in the presence of GAS6 (e.g., wherein the anti-AXL antibody or antigen-binding portion is at a concentration of 25 µg/mL or less and the GAS6 is at a concentration of 1 µg/mL),
 g) does not exhibit agonistic activity in the absence of GAS6 (e.g., at a concentration of up to 25 µg/mL),
 h) inhibits GAS6-induced uptake of phosphatidylserine-containing liposomes in MDA-MB-468-AXL cells stably expressing exogenous AXL (e.g., at a concentration of 6 µg/mL or less); and
 i) inhibits tumor growth in vivo (e.g., at a concentration of 10 mg/kg or 50 mg/kg).

In certain embodiments, the anti-AXL antibody or antigen-binding portion has at least properties a)-i). In certain embodiments, the anti-AXL antibody or antigen-binding portion has at least properties a)-e), and g)-i). In certain embodiments, the anti-AXL antibody or antigen-binding portion has at least properties a), b), e), g), and h). In certain embodiments, the anti-AXL antibody or antigen-binding portion has at least properties a)-e), g), and h). In certain embodiments, the anti-AXL antibody or antigen-binding portion has at least properties a)-e), g), and i).

In some embodiments, an anti-AXL antibody or antigen-binding portion described herein may inhibit tumor growth and/or induce tumor growth regression in vivo. In some embodiments, an anti-AXL antibody or antigen-binding portion described herein may slow down or reverse metastasis in a cancer patient. In some embodiments, an anti-AXL antibody or antigen-binding portion described herein may prolong survival of a cancer patient. Any combination of the above properties is also contemplated.

In certain embodiments, an antibody or antigen-binding portion thereof of the present disclosure may be part of a larger immunoadhesin molecule, formed by covalent or noncovalent association of the antibody or antibody portion with one or more other proteins or peptides. Examples of such immunoadhesin molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., *Mol. Immunol.* 31:1047-1058 (1994)). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another aspect, a fusion antibody or immunoadhesin may be made that comprises all or a portion of an anti-AXL antibody of the present disclosure linked to another polypeptide. In certain embodiments, only the variable domains of the anti-AXL antibody are linked to the polypeptide. In certain embodiments, the VH domain of an anti-AXL antibody is linked to a first polypeptide, while the VL domain of an anti-AXL antibody is linked to a second polypeptide that associates with the first polypeptide in a manner such that the VH and VL domains can interact with one another to form an antigen-binding site. In some embodiments, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence $(Gly_4\text{-}Ser)_3$ (SEQ ID NO: 64), such that the VH and VL sequences can be expressed as a contiguous single-chain protein, with the VL and VH domains joined by the flexible linker. See, e.g., Bird et al., Science 242:423-426 (1988); Huston et al., Proc. Natl. Acad. Sci. USA 85:5879-5883 (1988); and McCafferty et al., *Nature* 348:552-554 (1990). The single chain antibody may be monovalent, if only a single VH and VL are used; bivalent, if two VH and VL are used; or polyvalent, if more than two VH and VL are used. Bi-specific or polyvalent antibodies may be generated that bind specifically to human AXL and to another molecule, for instance.

In other embodiments, other modified antibodies may be prepared using anti-AXL antibody-encoding nucleic acid molecules. For instance, "kappa bodies" (Ill et al., Protein Eng. 10:949-57 (1997)), "minibodies" (Martin et al., EMBO J. 13:5303-9 (1994)), "diabodies" (Holliger et al., *Proc. Natl. Acad. Sci. USA* 90:6444-6448 (1993)), or "Janusins" (Traunecker et al., *EMBO J.* 10:3655-3659 (1991) and Traunecker et al., *Int. J. Cancer* (Suppl.) 7:51-52 (1992)) may be prepared using standard molecular biological techniques following the teachings of the specification.

An anti-AXL antibody or antigen-binding portion of the present disclosure can be derivatized or linked to another molecule (e.g., another peptide or protein). In general, the antibodies or portions thereof are derivatized such that AXL binding is not affected adversely by the derivatization or labeling. Accordingly, the antibodies and antibody portions of the present disclosure are intended to include both intact and modified forms of the human anti-AXL antibodies described herein. For example, an antibody or antibody portion of the present disclosure can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by cross-linking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, Ill.

An anti-AXL antibody or antigen-binding portion can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody or antigen-binding portion according to the present disclosure may also be labeled. As used herein, the terms "label" or "labeled" refer to incorporation of another molecule in the antibody. In some embodiments, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In certain embodiments, the antibodies of the present disclosure may be present in a neutral form (including zwitterionic forms) or as a positively or negatively-charged species. In some embodiments, the antibodies may be complexed with a counterion to form a pharmaceutically acceptable salt.

Anti-AXL Antibody Compositions

The present disclosure also provides a combination therapy (e.g., a composition) that comprises one, two, three, four, or more of the anti-AXL antibodies or antigen-binding portions thereof described herein. In certain embodiments, the combination therapy (e.g., composition) comprises two of the anti-AXL antibodies or antigen-binding portions. The combination therapy may take the form of, e.g., a method of treatment using said antibodies or antigen-binding portions or a pharmaceutical composition comprising said antibodies or antigen-binding portions.

In some embodiments, the present disclosure provides a composition comprising a first anti-AXL antibody or an antigen-binding portion thereof and a second anti-AXL antibody or an antigen-binding portion thereof, wherein the first and second antibodies are:

antibodies 23203_1 and 23203_2, respectively;
antibodies 23203_1 and 23203_3, respectively;
antibodies 23203_1 and 23203_4, respectively;
antibodies 23203_1 and 22995, respectively;
antibodies 23203_1 and 22883, respectively;
antibodies 23203_2 and 23203_3, respectively;
antibodies 23203_2 and 23203_4, respectively;
antibodies 23203_2 and 22995, respectively;
antibodies 23203_2 and 22883, respectively;
antibodies 23203_3 and 23203_4, respectively;
antibodies 23203_3 and 22995, respectively;
antibodies 23203_3 and 22883, respectively;
antibodies 23203_4 and 22995, respectively;
antibodies 23203_4 and 22883, respectively; or
antibodies 22995 and 22883, respectively.

In some embodiments, the composition comprises antibodies or antigen-binding portions thereof that bind to the same epitope as, or compete for binding with, said first and second antibodies.

In some embodiments, the composition comprises an antibody or an antigen-binding portion thereof that comprises the H-CDR1-3 and L-CDR1-3 amino acid sequences of said first antibody, and an antibody or an antigen-binding portion thereof that comprises the H-CDR1-3 and L-CDR1-3 amino acid sequences of said second antibody.

In some embodiments, the composition comprises an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical to the VH and VL amino acid sequences, respectively, of said first antibody, and an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical to the VH and VL amino acid sequences, respectively, of said second antibody.

In some embodiments, the composition comprises an antibody or an antigen-binding portion thereof that comprises the VH and VL amino acid sequences of said first antibody, and an antibody or an antigen-binding portion thereof that comprises the VH and VL amino acid sequences of said second antibody.

In some embodiments, the composition comprises an antibody or an antigen-binding portion thereof that comprises the HC and LC amino acid sequences of said first antibody, and an antibody or an antigen-binding portion thereof that comprises the HC and LC amino acid sequences of said second antibody.

In certain embodiments, said composition may comprise one, two, or more antibodies or antigen-binding portions thereof selected from the group consisting of:
a) an antibody comprising H-CDR1-3 that comprise the amino acid sequences of SEQ ID NOs: 5-7, 15-17, 25-27, 35-37, 45-47, or 55-57, respectively;
b) an antibody whose VH is at least 90% identical in sequence to the amino acid sequence of SEQ ID NO: 3, 13, 23, 33, 43, or 53;
c) an antibody whose VH comprises the amino acid sequence of SEQ ID NO: 3, 13, 23, 33, 43, or 53;
d) an antibody whose HC comprises the amino acid sequences of SEQ ID NOs: 3 and 61, 13 and 61, 23 and 61, 33 and 61, 43 and 61, or 53 and 61;
e) an antibody comprising L-CDR1-3 that comprise the amino acid sequences of SEQ ID NOs: 8-10, 18-20, 28-30, 38-40, 48-50, or 58-60, respectively;
f) an antibody whose VL is at least 90% identical in sequence to the amino acid sequence of SEQ ID NO: 4, 14, 24, 34, 44, or 54;
g) an antibody whose VL comprises the amino acid sequence of SEQ ID NO: 4, 14, 24, 34, 44, or 54;
h) an antibody whose LC comprises the amino acid sequences of SEQ ID NOs: 4 and 62, 14 and 62, 24 and 62, 34 and 62, 44 and 62, or 54 and 62;
i) an antibody whose H-CDR1-3 and L-CDR1-3 comprise the amino acid sequences of SEQ ID NOs: 5-10, 15-20, 25-30, 35-40, 45-50, or 55-60, respectively;
j) an antibody comprising VH and VL that comprise amino acid sequences at least 90% identical to the amino acid sequences of SEQ ID NOs: 3 and 4, 13 and 14, 23 and 24, 33 and 34, 43 and 44, or 53 and 54, respectively;
k) an antibody comprising VH and VL that comprise the amino acid sequences of SEQ ID NOs: 3 and 4, 13 and 14, 23 and 24, 33 and 34, 43 and 44, or 53 and 54, respectively; and
l) an antibody comprising HC and LC that comprise the amino acid sequences of 3 and 61, and 4 and 62; 13 and 61, and 14 and 62; 23 and 61, and 24 and 62; 33 and 61, and 34 and 62; 43 and 61, and 44 and 62; or 53 and 61, and 54 and 62; respectively.

In some embodiments, an anti-AXL antibody composition described herein may inhibit tumor growth and/or induce tumor growth regression in vivo. In some embodiments, an anti-AXL antibody composition described herein may prolong survival of a cancer patient.

The present disclosure also provides a method for producing an anti-AXL antibody composition described herein, comprising providing a first anti-AXL antibody or antigen-binding portion and a second anti-AXL antibody or antigen-binding portion, and admixing the two antibodies or portions.

Bi-Specific Binding Molecules

The present disclosure also provides a bi-specific binding molecule having the binding specificity (e.g., comprising the antigen-binding portions, such as the six CDRs or the VH and VL) of an anti-AXL antibody described herein. In some embodiments, the bi-specific binding molecule additionally has the binding specificity of another, distinct anti-AXL antibody (e.g., another anti-AXL antibody described herein) or an antibody that targets a different protein, such as a cancer antigen or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

The present disclosure also provides nucleic acid molecules and sequences encoding anti-AXL antibodies or antigen-binding portions thereof described herein. In some embodiments, different nucleic acid molecules encode the heavy chain and light chain amino acid sequences of the anti-AXL antibody or antigen-binding portion. In other embodiments, the same nucleic acid molecule encodes the heavy chain and light chain amino acid sequences of the anti-AXL antibody or antigen-binding portion.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

In some embodiments, the present disclosure provides a nucleic acid molecule comprising a nucleotide sequence that encodes the heavy chain or an antigen-binding portion thereof, or a nucleotide sequence that encodes the light chain or an antigen-binding portion thereof, or both, of an anti-AXL antibody or antigen-binding portion thereof described herein.

The present disclosure also provides nucleotide sequences that are at least 70%, 75%, 80%, 85%, 90%, 95%, 97%, 98% or 99% identical to one or more nucleotide sequences recited herein, e.g., to a nucleotide sequence selected from the group consisting of SEQ ID NOs: 1, 2, 11, 12, 21, 22, 31, 32, 41, 42, 51, and 52, or to a nucleotide sequence encoding an amino acid sequence selected from the group consisting of SEQ ID NOs: 3, 4, 13, 14, 23, 24, 33, 34, 43, 44, 53, and 54. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wis. FASTA, which includes, e.g., the programs FASTA2 and FASTA3, provides alignments and percent sequence identity of the regions of the best overlap between the query and search sequences (see, e.g., Pearson, *Methods Enzymol.* 183:63-98 (1990); Pearson, *Methods Mol. Biol.* 132:185-219 (2000); Pearson, *Methods Enzymol.* 266:227-258 (1996); and Pearson, *J. Mol. Biol.* 276:71-84 (1998); incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In some embodiments, the present disclosure provides a nucleic acid molecule comprising a nucleotide sequence selected from the group consisting of SEQ ID NOs: 1, 2, 11, 12, 21, 22, 31, 32, 41, 42, 51, and 52. In certain embodiments, the nucleic acid molecule comprises the nucleotide sequences of SEQ ID NOs: 1 and 2, 11 and 12, 21 and 22, 31 and 32, 41 and 42, or 51 and 52.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In a further aspect, the present disclosure provides a vector suitable for expressing one or both of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. Moreover, certain vectors are capable of directing the expression of genes to which they are operatively linked. Such vectors are referred to herein as "recombinant expression vectors" (or simply, "expression vectors").

The present disclosure provides vectors comprising nucleic acid molecules that encode the heavy chain, the light chain, or both the heavy and light chains of an anti-AXL antibody as described herein or an antigen-binding portion thereof. In certain embodiments, a vector of the present disclosure comprises a nucleic acid molecule described herein. The present disclosure further provides vectors comprising nucleic acid molecules encoding fusion proteins, modified antibodies, antibody fragments, and probes thereof. The vector may further comprise an expression control sequence.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

In some embodiments, a nucleic acid molecule as described herein comprises a nucleotide sequence encoding a VH domain from an anti-AXL antibody or antigen-binding portion as described herein joined in-frame to a nucleotide sequence encoding a heavy chain constant region from any source. Similarly, a nucleic acid molecule as described herein can comprise a nucleotide sequence encoding a VL domain from an anti-AXL antibody or antigen-binding portion as described herein joined in-frame to a nucleotide sequence encoding a light chain constant region from any source.

In a further aspect of the present disclosure, nucleic acid molecules encoding the VH and/or VL may be "converted" to full-length antibody genes. In some embodiments, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another aspect, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL region using standard molecular biological techniques. Nucleic acid molecules encoding the full-length heavy and/or light chains may then be expressed from a cell into which they have been introduced and the anti-AXL antibody isolated.

In some embodiments, the framework region(s) are mutated so that the resulting framework region(s) have the amino acid sequence of the corresponding germline gene. A mutation may be made in a framework region or constant region, e.g., to increase the half-life of the anti-AXL antibody. See, e.g., PCT Publication WO 00/09560. A mutation in a framework region or constant region also can be made to alter the immunogenicity of the antibody, and/or to provide a site for covalent or non-covalent binding to another molecule. According to the present disclosure, an antibody may have mutations in any one or more of the CDRs or framework regions of the variable domain or in the constant region.

Host Cells and Methods of Antibody and Antibody Composition Production

The present disclosure also provides methods for producing the antibody compositions and antibodies and antigen-binding portions thereof described herein. In some embodiments the present disclosure relates to a method for producing an anti-AXL antibody or antigen-binding portion as described herein, comprising providing a host cell (e.g., a recombinant host cell) comprising a nucleotide sequence that encodes the heavy chain or an antigen-binding portion thereof, and a nucleotide sequence that encodes the light chain or an antigen-binding portion thereof, of an anti-AXL antibody or antigen-binding portion described herein; cultivating said host cell under conditions suitable for expression of the antibody or antigen-binding portion; and isolating the resulting antibody or antigen-binding portion. Antibodies or antigen-binding portions produced by such expression in such recombinant host cells are referred to herein as "recombinant" antibodies or antigen-binding portions. The present disclosure also provides progeny cells of such host cells, and antibodies or antigen-binding portions produced by same.

The term "recombinant host cell" (or simply "host cell"), as used herein, means a cell into which a recombinant expression vector has been introduced. By definition, a recombinant host cell does not occur in nature. The present disclosure provides host cells that may comprise, e.g., a vector as described herein. The present disclosure also provides host cells that comprise, e.g., a nucleotide sequence encoding the heavy chain or an antigen-binding portion thereof, a nucleotide sequence encoding the light chain or an antigen-binding portion thereof, or both, of an anti-AXL antibody or antigen-binding portion thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-AXL antibodies and antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

It is likely that antibodies expressed by different cell lines or in transgenic animals will have different glycosylation patterns from each other. However, all antibodies encoded by the nucleic acid molecules provided herein, or comprising the amino acid sequences provided herein are part of the present disclosure, regardless of the glycosylation state of the antibodies, and more generally, regardless of the presence or absence of post-translational modification(s).

Pharmaceutical Compositions

Another aspect of the present disclosure is a pharmaceutical composition comprising as an active ingredient (or as the sole active ingredient) an anti-AXL antibody or antigen-binding portion thereof, antibody composition, or bi-specific binding molecule of the present disclosure. The pharmaceutical composition may additionally comprise a pharmaceutically acceptable excipient. In some embodiments, the pharmaceutical compositions are intended for amelioration, prevention, and/or treatment of cancer, e.g., a cancer described herein. In certain embodiments, the cancer is in a tissue such as skin, lung, intestine, colon, ovary, brain, prostate, kidney, soft tissues, the hematopoietic system, head and neck, liver, bone, bladder, breast, stomach, uterus, cervix, and pancreas. In certain embodiments, the cancer is melanoma, head and neck cancer, glioblastoma, thyroid cancer, non-small cell lung cancer, breast cancer (e.g., triple negative breast cancer), pancreatic cancer, ovarian cancer, cervical cancer, fallopian tube carcinoma, primary peritoneal carcinoma, endometrial cancer, urothelial carcinoma, renal cell carcinoma, colorectal cancer, rectal cancer, prostate cancer, mesothelioma, squamous cell carcinoma, sarcoma, chronic myeloid leukemia, acute myeloid leukemia, chronic lymphocytic leukemia, small lymphocytic leukemia, myelodysplastic syndrome, or Hodgkin's lymphoma.

Pharmaceutical compositions of the present disclosure will comprise one or more anti-AXL antibodies, antigen-binding portions, antibody compositions, or bi-specific binding molecules of the present disclosure, e.g., one or two anti-AXL antibodies, antigen-binding portions, or bi-specific binding molecules. In some embodiments, the composition comprises a single anti-AXL antibody of the present disclosure or an antigen-binding portion thereof. In another aspect, the composition comprises two distinct anti-AXL antibodies of the present disclosure or antigen-binding portions thereof.

In some embodiments, the pharmaceutical composition may comprise at least one anti-AXL antibody or antigen-binding portion thereof of the present disclosure, e.g., one anti-AXL antibody or portion, and one or more additional antibodies that target one or more relevant cell surface receptors, e.g., one or more cancer-relevant receptors.

Generally, the antibodies, antigen-binding portions, and bi-specific binding molecules of the present disclosure are suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present disclosure and methods for their preparation will be readily apparent to those skilled in the art. Such compositions and methods for their preparation may be found, for example, in *Remington's Pharmaceutical Sciences*, 19th Edition (Mack Publishing Company, 1995). Pharmaceutical compositions are preferably manufactured under GMP (good manufacturing practices) conditions.

A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation.

Therapeutic Uses of Antibodies and Compositions of the Present Disclosure

In some embodiments, the anti-AXL antibodies and antigen-binding portions thereof, anti-AXL antibody compositions, and bi-specific binding molecules of the present disclosure are for use in the treatment of cancer, e.g., an AXL-positive cancer. The cancer may be in one or more tissues such as skin, lung, intestine, colon, ovary, brain, prostate, kidney, soft tissues, the hematopoietic system, head and neck, liver, bone, bladder, breast, stomach, uterus, cervix, and pancreas.

In some embodiments, cancers treated by the anti-AXL antibodies, antigen-binding portions, compositions, and bi-specific binding molecules of the present disclosure may include, e.g., melanoma (e.g., advanced or metastatic melanoma), skin basal cell cancer, glioblastoma, glioma, gliosarcoma, astrocytoma, meningioma, neuroblastoma, adrenocortical cancer, head and neck squamous cell cancer, oral cancer, salivary gland cancer, nasopharyngeal cancer, breast cancer, lung cancer (e.g., non-small cell lung cancer (NSCLC), small cell lung cancer, and squamous cell lung cancer), esophageal cancer, gastroesophageal junction cancer, gastric cancer, gastrointestinal cancer, primary peritoneal cancer, liver cancer, hepatocellular carcinoma, biliary tract cancer, colon cancer, rectal cancer, colorectal carcinoma, ovarian cancer, fallopian tube cancer, bladder cancer, upper urinary tract cancer, urothelial cancer, renal cell carcinoma, kidney cancer, genitourinary cancer, cervical cancer, prostate cancer, fibrosarcoma, liposarcoma, rhabdomyosarcoma, osteosarcoma, histiocytoma, pancreatic cancer, endometrial cancer, cancer of the appendix, advanced Merkel cell cancer, multiple myeloma, sarcomas, choriocarcinoma, erythroleukemia, acute lymphoblastic leukemia, acute monocytic leukemia, acute promyelocytic leukemia, acute myeloid leukemia, chronic myeloid leukemia, chronic lymphocytic leukemia, acute lymphoblastic leukemia, mast cell leukemia, small lymphocytic lymphoma, Burkitt's lymphoma, Hodgkin's lymphoma, non-Hodgkin's lymphoma, diffuse large B cell lymphoma, follicular lymphoma, monocytic lymphoma, HTLV-associated T cell leukemia/lymphoma, mesothelioma, and solid tumors. The cancer may be, e.g., at an early, intermediate, late, locally advanced, or metastatic stage, and may be relapsed or refractory to other therapeutics (e.g., other anti-AXL therapeutics) or there may be no standard therapy available.

In some embodiments, cancers treated by the anti-AXL antibodies, antigen-binding portions, compositions, and/or bi-specific binding molecules of the present disclosure may include, e.g., melanoma, head and neck cancer, glioblastoma, thyroid cancer, non-small cell lung cancer, breast cancer (e.g., triple negative breast cancer), pancreatic cancer, ovarian cancer, cervical cancer, fallopian tube carcinoma, primary peritoneal carcinoma, endometrial cancer, urothelial carcinoma, renal cell carcinoma, colorectal cancer, prostate cancer, mesothelioma, squamous cell carcinoma, sarcoma, chronic myeloid leukemia, acute myeloid leukemia, chronic lymphocytic leukemia, small lymphocytic leukemia, myelodysplastic syndrome, and/or Hodgkin's lymphoma.

"Treat," "treating," and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in delayed tumor growth, tumor shrinkage, increased survival, elimination of cancer cells, slowed or decreased disease progression, reversal of metastasis, or other clinical endpoints desired by healthcare professionals.

The anti-AXL antibodies or antigen-binding portions thereof, antibody compositions, or bi-specific binding molecules described herein may be administered alone or in combination with one or more other drugs or antibodies (or as any combination thereof). The pharmaceutical compositions, methods and uses described herein thus also encompass embodiments of combinations (co-administration) with other active agents, as detailed below.

As used herein, the terms "co-administration," "co-administered" and "in combination with," referring to the anti-AXL antibodies and antigen-binding portions thereof, antibody compositions, and bi-specific binding molecules of the present disclosure with one or more other therapeutic agents, is intended to mean, and does refer to and include the following:

a) simultaneous administration of such combination of antibody/antigen-binding portion/antibody composition/bi-specific binding molecule of the present disclosure and therapeutic agent(s) to a patient in need of treatment, when such components are formulated together into a single dosage form which releases said components at substantially the same time to said patient, b) substantially simultaneous administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at substantially the same time by said patient, whereupon said components are released at substantially the same time to said patient, c) sequential administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and d) sequential administration of such combination of antibody/antigen-binding portion/antibody composition/bi-specific binding molecule of the present disclosure and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The anti-AXL antibodies or antigen-binding portions thereof, antibody compositions, or bi-specific binding molecules of the present disclosure may be administered without additional therapeutic treatments, i.e., as a stand-alone therapy (monotherapy). Alternatively, treatment with the anti-AXL antibodies or antigen-binding portions thereof, antibody compositions, or bi-specific binding molecules of the present disclosure may include at least one additional therapeutic treatment (combination therapy), e.g., an immunostimulatory agent, an anti-cancer agent (e.g., a chemotherapeutic agent, an anti-neoplastic agent, an anti-angiogenic agent, or a tyrosine kinase inhibitor), or a vaccine (e.g., a tumor vaccine).

In some aspects, the antibody or antigen-binding portion thereof, antibody composition, or bi-specific binding molecule may be co-administered or formulated with another medication/drug for the treatment of cancer. The additional therapeutic treatment may comprise, e.g., an immunostimulatory agent, a vaccine, a chemotherapeutic agent, an anti-neoplastic agent, an anti-angiogenic agent, a tyrosine kinase inhibitor, and/or radiation therapy. In some embodiments, the additional therapeutic treatment may comprise a different anti-cancer antibody, Pharmaceutical articles comprising an anti-AXL antibody or antigen-binding portion thereof, antibody composition, or bi-specific binding molecule described herein and at least one other agent (e.g., a chemotherapeutic, anti-neoplastic, or anti-angiogenic agent) may be used as a combination treatment for simultaneous, separate or successive administration in cancer therapy. The other agent may by any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; antimetabolites, e.g., fluorouracil and/or other fluoropyrimidines; FOLFOX; osimertinib; cyclophosphamide; anthracycline; dacarbazine; gemcitabine; or any combination thereof. In some embodiments, the anti-AXL antibody or antigen-binding portion thereof, antibody composition, or bi-specific binding molecule described herein reestablishes responsiveness to the other agent.

An anti-AXL antibody or antigen-binding portion thereof, antibody composition, or bi-specific binding molecule of the present disclosure may also be used in combination with other anti-cancer therapies such as vaccines, cytokines, enzyme inhibitors, immunostimulatory compounds, and T cell therapies. In the case of a vaccine, it may be, e.g., a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example, 1-methyl-D-tryptophan (1-D-MT). Also contemplated is adoptive T cell therapy, which refers to various immunotherapy techniques that involve expanding or engineering patients' own T cells to recognize and attack their tumors.

It is also contemplated that an anti-AXL antibody or antigen-binding portion thereof, antibody composition, or bi-specific binding molecule of the present disclosure may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation, e.g., by competing for the intracellular Mg-ATP binding site. In some embodiments, the tyrosine kinase inhibitor is an AXL inhibitor.

In some embodiments, the antibody or antigen-binding portion thereof, antibody composition, or bi-specific binding molecule may be used in combination with a medication/ drug that mediates immune system activation, including, but not limited to, an agent that modulates the expression or activity of A2AR, A1AR, A2BR, A3AR, ADA, ALP, BTLA, B7-H3, B7-H4, CTLA-4, CD27, CD28, CD39, CD40, CD47, CD55, CD73, CD122, CD137, CD160, CGEN-15049, CHK1, CHK2, CTLA-3, CEACAM (e.g., CEACAM-1 and/or CEACAM-5), EGFR, FLT3, FLT3L, GAL9, GITR, HVEM, LAG-3, LILRB1, LY108, LAIR1, ICOS, IDO, KIR, LAIR1, MET, NKG2A, PAP, PD-1/PD-L1/PD-L2, OX40, STING, TIGIT, TIM-3, TGFR-beta, TLR, TNFR2, VEGF, VEGFR, VISTA, LILRB2, CMTM6 and/or 2B4. In certain embodiments, the agent is a small molecule inhibitor. In certain embodiments, the agent is an antibody or an antigen-binding fragment thereof that binds to one of the above molecules. It is also contemplated that an anti-AXL antibody or antigen-binding portion thereof, antibody composition, or bi-specific binding molecule of the present disclosure may be used in combination with a cytokine (e.g., IL-1, IL-2, IL-12, IL-15 or IL-21), an EGFR inhibitor, a VEGF inhibitor, etc.

The present disclosure also contemplates the use of sequences (e.g., the six CDR or VH and VL sequences) of an anti-AXL antibody or antigen-binding portion described herein in the preparation of a chimeric antigen receptor, which may be for use in CAR-T technology.

It is understood that the antibodies and antigen-binding portions thereof, antibody compositions, and bi-specific binding molecules of the present disclosure may be used in a method of treatment as described herein, may be for use in a treatment as described herein, and/or may be for use in the manufacture of a medicament for a treatment as described herein.

Dose and Route of Administration

The antibodies or antigen-binding portions thereof, antibody compositions, or bi-specific binding molecules of the present disclosure may be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the present disclosure are generally dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of the present disclosure may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining of appropriate dosages and regimens is well-known in the relevant art and would be understood to be encompassed by the skilled artisan once provided the teachings disclosed herein.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, antibody composition, or bi-specific binding molecule of the present disclosure to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

The antibodies or antigen-binding portions thereof, antibody compositions, or bi-specific binding molecules of the present disclosure may be administered by any method for administering peptides, proteins or antibodies accepted in the art, and are typically suitable for parenteral administration. As used herein, "parenteral administration" includes any route of administration characterized by physical breaching of a tissue of a subject and administration through the breach in the tissue, thus generally resulting in the direct administration into the blood stream, into muscle, or into an internal organ. Parenteral administration thus includes, but is not limited to, administration by injection, by application through a surgical incision, by application through a tissue-penetrating non-surgical wound, and the like. In particular, parenteral administration is contemplated to include, but is not limited to, subcutaneous, intraperitoneal, intramuscular, intrasternal, intracisternal, intravenous, intraarterial, intrathecal, intraurethral, intracranial, intratumoral, and intrasynovial injection or infusions. Particular embodiments include the intravenous and the subcutaneous routes.

Diagnostic Uses and Compositions

The antibodies and antigen-binding portions of the present disclosure also are useful in diagnostic processes (e.g., in vitro, ex vivo). For example, the antibodies and antigen-binding portions can be used to detect and/or measure the level of AXL in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassays, and immunohistology. The present disclosure further encompasses kits (e.g., diagnostic kits) comprising the antibodies and antigen-binding portions described herein.

Articles of Manufacture and Kits

The present disclosure also provides articles of manufacture, e.g., kits, comprising one or more containers (e.g., single-use or multi-use containers) containing a pharmaceutical composition of an anti-AXL antibody or antigen-binding portion thereof, composition, or bi-specific binding molecule described herein, optionally an additional biologically active molecule (e.g., another therapeutic agent), and instructions for use. The antibody or antigen-binding portion, composition, or bi-specific binding molecule, and optional additional biologically active molecule, can be packaged separately in suitable packing such as a vial or ampule made from non-reactive glass or plastic. In certain embodiments, the vial or ampule holds a concentrated stock (e.g., 2x, 5x, 10x or more) of the antibody or antigen-binding portion, composition, or bi-specific binding molecule and optionally the biologically active molecule. In certain embodiments, the articles of manufacture such as kits include a medical device for administering the antibody or antigen-binding portion, composition, or bi-specific binding molecule and/or biologically active molecule (e.g., a syringe and a needle); and/or an appropriate diluent (e.g., sterile water and normal saline). The present disclosure also includes methods for manufacturing said articles.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that the present disclosure may be better understood, the following examples are set forth. These examples are for purposes of illustration only and are not to be construed as limiting the scope of the present disclosure in any manner.

EXAMPLES

Example 1: Cloning of Anti-AXL Antibodies from Rat B Cells

Materials and Methods

Antibodies against human AXL were isolated from an antibody repertoire derived from OmniRat® rats (Osborn et al., *J Immunol.* 190(4):1481-90 (2013)), a transgenic rat strain from Ligand Pharmaceuticals Inc. that produces antibodies with fully human idiotypes. Cloning of rat-derived antibody genes from single-cell sorted antibody-secreting B cells (ASC) was performed by means of Symplex™ antibody discovery technology (Meijer et al., *J Mol Biol* 358 (3):764-72 (2006)).

Antibody repertoire constructs encoding fully human immunoglobulins in $IgG_1$-LALA format (see below) were transfected into HEK293 cells. Cell supernatants were screened for binding to AXL expressed on the surface of CHO cells using flow cytometry in a high-throughput format. AXL reactive clones were analyzed by DNA sequencing and antibody-encoding DNA sequences were extracted. Selected antibody clones were expressed and tested functionally as described below.

Missense mutations in the amino termini of heavy and light chains that were introduced by the use of degenerate primers in the Symplex™ cloning of the antibody-encoding cDNA fragments were corrected back to germline sequence. Table 1 shows the heavy and light chain variable domain nucleotide sequences of the germlined antibodies designated 23203_1, 23203_2, 23203_3, 23203_4, 22995, and 22883. The correction process involved amino terminal sequence correction to germline as well as codon usage optimization. The targets for matching to human germline sequences were identified by blast homology searches for the heavy chain and the light chain variable regions.

Antibodies 23203_1, 23203_2, 23203_3, and 23203_4 represent four variants of a single parent heavy chain variable domain that has been engineered to mitigate potential risks associated with the germline IGHV4-34 sequence (i.e., the AVY motif of HFR1 and the Nglyc site in HCDR2).

Protein sequences of the variable domains, the constant regions and the complementarity determining regions (CDR) of antibodies 23203_1, 23203_2, 23203_3, 23203_4, 22995, and 22883 are shown in Table 2, Table 3 and Table 4, respectively.

Results

Table 1 shows nucleotide sequences encoding the variable domains of antibodies 23203_1, 23203_2, 23203_3, 23203_4, 22995, and 22883.

TABLE 1

Variable domain nucleotide sequences of antibodies
23203_1, 23203_2, 23203_3, 23203_4, 22995, and 22883

| Ab | Sequence (5' to 3') |
| --- | --- |
| 23203_1 VH SEQ ID NO: 1 | CAGGTGCAGCTGCAGGAGTCTGGCCCTGGCCTGGTGAAGCCAAGCGAGACACTGT CTCTGACCTGTACCGTGTCTGGCGGCTCTTTTTCTGGATATTACTGGAGCTGGAT CAGACAGCCACCCGGCAAGGGCCTGGAGTGGATCGGCGAGATCAACCACGCTGGC TCCACCAATTACAACCCCTCTCTGAAGAGCAGAGTGACCATCTCTGTGGATACCT CCAAGAACCAGTTCTCCCTGAAGCTGTCTAGCGTGACAGCCGCTGATACAGCCGT GTACTATTGCTCTTCCCGCGAGTACTCCTCTCGTTGGCACTTCGACTACTGGGGC CAGGGCACACTGGTGACCGTCTCGAGT |
| 23203_1 VL SEQ ID NO: 2 | GATATCCAGCTGACCCAGTCCCCTAGCTTCCTGTCTGCTTCCGTGGGCGATAGAG TGACCATCACATGTAGAGCCTCTCAGGGCATCTCCTCTTACCTGGCTTGGTATCA GCAGAAGCCTGGCAAGGCTCCTAAGCTGCTGATCTATGCTGCCTCTACACTGCAG TCTGGCGTGCCATCCCGGTTCAGCGGCTCTGGCAGCGGCACCGAGTTCACACTGA CCATCTCCTCTCTGCAGCCAGAGGATTTCGCTACCTACTATTGCCAGCAGCTGAA CAGCTACCCTCTGACATTTGGCGGCGGCACAAAGGTGGAGATCAAG |
| 23203_2 VH SEQ ID NO: 11 | CAGGTGCAGCTGCAGCAGTGGGGCGCTGGCCTGCTGAAGCCTTCTGAGACACTGT CTCTGACCTGTGCCGTGTATGGCGGCTCTTTTTCGGGCTATTACTGGACCTGGAT CAGACAGCCCTCCAGGCAAGGGCCTGGAGTGGATCGGCGAGATCAATCACTCCGGC TCTACCAACTACAATCCATCCCTGAAGAGCAGAGTGACCATCTCCGTGGATACCT CCAAGAATCAGTTTTCTCTGAAGCTGTCCTCTGTGACAGCTGCTGATACCGCCGT GTACTATTGCTCTAGCAGAGAGTACTCCTCTAGATGGCACTTCGATTACTGGGGC CAGGGCACACTGGTGACCGTCTCGAGT |
| 23203_2 VL SEQ ID NO: 12 | GATATCCAGCTGACCCAGTCCCCTAGCTTCCTGTCTGCTTCCGTGGGCGATAGAG TGACCATCACATGTAGAGCCTCTCAGGGCATCTCCTCTTACCTGGCTTGGTATCA GCAGAAGCCTGGCAAGGCTCCTAAGCTGCTGATCTATGCTGCCTCTACACTGCAG TCTGGCGTGCCATCCCGGTTCAGCGGCTCTGGCAGCGGCACCGAGTTCACACTGA CCATCTCCTCTCTGCAGCCAGAGGATTTCGCTACCTACTATTGCCAGCAGCTGAA CAGCTACCCTCTGACATTTGGCGGCGGCACAAAGGTGGAGATCAAG |
| 23203_3 VH SEQ ID NO: 21 | CAGGTGCAGCTGCAGCAGTGGGGCGCTGGCCTGCTGAAGCCTTCTGAGACACTGT CTCTGACCTGTACCGTGTCTGGCGGCTCTTTTTTCCGGCTATTACTGGACCTGGAT CAGGCAGCCACCTGGCAAGGGCCTGGAGTGGATCGGCGAGATCAACCACGCTGGC TCCACCAACTACAATCCTTCCCTGAAGTCTAGAGTGACCATCTCCGTGGATACCT CCAAGAACCAGTTCTCCCTGAAGCTGTCCTCTGTGACCGCCGCTGATACAGCCGT GTACTATTGCTCCAGCAGAGAGTACTCCTCTAGATGGCACTTCGACTACTGGGGC CAGGGCACACTGGTGACAGTCTCGAGT |
| 23203_3 VL SEQ ID NO: 22 | GATATCCAGCTGACCCAGTCCCCTAGCTTCCTGTCTGCTTCCGTGGGCGATAGAG TGACCATCACATGTAGAGCCTCTCAGGGCATCTCCTCTTACCTGGCTTGGTATCA GCAGAAGCCTGGCAAGGCTCCTAAGCTGCTGATCTATGCTGCCTCTACACTGCAG TCTGGCGTGCCATCCCGGTTCAGCGGCTCTGGCAGCGGCACCGAGTTCACACTGA CCATCTCCTCTCTGCAGCCAGAGGATTTCGCTACCTACTATTGCCAGCAGCTGAA CAGCTACCCTCTGACATTTGGCGGCGGCACAAAGGTGGAGATCAAG |
| 23203_4 VH SEQ ID NO: 31 | CAGGTGCAGCTGCAGCAGTGGGGCGCTGGCCTGCTGAAGCCTTCTGAGACACTGT CTCTGACCTGTGCCGTGTATGGCGGCTCTTTTTTCCGGCTATTACTGGACCTGGAT CAGGCAGCCACCTGGCAAGGGCCTGGAGTGGATCGGCGAGATCAACCACGCTGGC TCCACCAACTACAATCCTTCCCTGAAGTCTAGAGTGACCATCTCCGTGGATACCT CCAAGAACCAGTTCTCCCTGAAGCTGTCCTCTGTGACCGCCGCTGATACAGCCGT GTACTATTGCTCCAGCAGAGAGTACTCCTCTAGATGGCACTTCGACTACTGGGGC CAGGGCACACTGGTGACAGTCTCGAGT |
| 23203_4 VL SEQ ID NO: 32 | GATATCCAGCTGACCCAGTCCCCTAGCTTCCTGTCTGCTTCCGTGGGCGATAGAG TGACCATCACATGTAGAGCCTCTCAGGGCATCTCCTCTTACCTGGCTTGGTATCA GCAGAAGCCTGGCAAGGCTCCTAAGCTGCTGATCTATGCTGCCTCTACACTGCAG TCTGGCGTGCCATCCCGGTTCAGCGGCTCTGGCAGCGGCACCGAGTTCACACTGA CCATCTCCTCTCTGCAGCCAGAGGATTTCGCTACCTACTATTGCCAGCAGCTGAA CAGCTACCCTCTGACATTTGGCGGCGGCACAAAGGTGGAGATCAAG |
| 22995 VH SEQ ID NO: 41 | GAGGTGCAGCTGGTGGAGTCTGGCGGCAGCCTGGTGCAGCCCGGCGGCTCTCTGA GACTGTCTTGTGCCGCTTCTGGCTTTACCTTCTCTTCATCCGCTATGTCTTGGGT GCGCCAAGCCCCAGGCAAGGGCCTGGAGTGGGTGTCTACCATCTCCGGCAGCGAT TCTTCCACCTACGACGCTGATTCCGTGAAGGGCAGAAGCACAATCTCCAGGGACA ATTCCAAGAACACCCTGTATCTGCAGATGAACTCCCTGAGAGCTGATGACACCGC CGTGTATTACTGCGCTAAGAAGGGCGCTTATTGTTCCGGCACAATCTGCTACGAT CCCTTCGACTATTGGGGCCAGGGCACACTGGTGACCGTCTCGAGT |
| 22995 VL SEQ ID NO: 42 | GATATCGTGCTGACCCAGTCTCCAGTGCTGGCCGTGTCCCTGGGCCAGAGAGCTA CCATCTCTTGCAGAGCTTCTCAGTCCGTGTCTATCAGCTCCATCAACCTGATGCA TTGGTACCAGCAGAAGCCAGGCCAGCAGCCAAAGCTGCTGATCTACAGAGCCAGC AACCTGGCTTCTGGCATCCCAGCTAGATTCTCCGGCTCTGGCAGCGGCACAGATT TCACCCTGACAATCGATCCTGTGCAGGCTGACGATATCGCCGCTTATTACTGCCA GCAGTCCAGAGAGTCTCCTCTGACCTTTGGCGGCGGCACAAAGGTGGAGATCAAG |

TABLE 1-continued

Variable domain nucleotide sequences of antibodies
23203_1, 23203_2, 23203_3, 23203_4, 22995, and 22883

| Ab | Sequence (5' to 3') |
|---|---|
| 22883 VH<br>SEQ ID NO: 51 | GAGGTGCAGCTGGTGGAGTCTGGCGGCGGCCTGGTGCAGCCAGGCGGCTCTCTGA<br>GACTGTCTTGTGCCGCTTCTGGCTTTACCTTCTCCTCTTACGCCATGTCTTGGGT<br>GCGGCAAGCCCCCGGCAAGGGCCTGGAGTGGGTGTCTGCTATCTCCGGCGGCGGC<br>GACTATACCTACTATGCCGACAGCGTGAAGGGCAGATTCACCATCAGCAGGGACA<br>ATTCCAAGAACACCCTGTACCTGCAGATGAACTCCCTGAGAGCTGAGGATACAGC<br>CGTGTACTATTGCGCCAAGGAGGAGTGGGAGCTGAGAGGCCCATTTCGGTATTGG<br>GGCCAGGGCACACTGGTGACAGTCTCGAGT |
| 22883 VL<br>SEQ ID NO: 52 | GACATCCAGATGACCCAGAGCCCTTCCACCCTGAGCGCCAGCGTCGGAGATAGAG<br>TGACAATTACTTGCCGTGCCAGCCAGTCCATTTCCTCTTGGCTGGCCTGGTACCA<br>GCAGAAGCCTGGCAAGGCCCCTAAGTTCCTGATCTATAAAGCTTCTTCCCTGGAG<br>TCTGGAGTCCCATCCAGGTTCTCCGGCTCTGGATCCGGAACCGAGTTTACCCTGA<br>CAATCAGCTCTCTGCAGCCCGACGATTTTGCCACATACTATTGTCAGCAGTATAA<br>CGGGTTTAGTTGGACCTTCGGGCAGGGCACAAAAGTGGAGATCAAA |

Table 2 shows the deduced amino acid sequences of antibodies 23203_1, 23203_2, 23203_3, 23203_4, 22995, 22883. CDRs are in boldface and underlined.

TABLE 2

Variable domain amino acid sequences of antibodies
23203_1, 23203_2, 23203_3, 23203_4, 22995, and 22883.

| Ab | Sequence (N-terminus to C-terminus) |
|---|---|
| 23203_1 VH<br>SEQ ID NO: 3 | QVQLQESGPGLVKPSETLSLTCTVSGGSFSGYYWSWIRQPPGKGLEWIGEINHAG<br>STNYNPSLKSRVTISVDTSKNQFSLKLSSVTAADTAVYYCSSREYSSRWHFDYWG<br>QGTLVTVSS |
| 23203_1 VL<br>SEQ ID NO: 4 | DIQLTQSPSFLSASVGDRVTITCRASQGISSYLAWYQQKPGKAPKLLIYAASTLQ<br>SGVPSRFSGSGSGTEFTLTISSLQPEDFATYYCQQLNSYPLTFGGGTKVEIK |
| 23203_2 VH<br>SEQ ID NO: 13 | QVQLQQWGAGLLKPSETLSLTCAVYGGSFSGYYWTWIRQPPGKGLEWIGEINHSG<br>STNYNPSLKSRVTISVDTSKNQFSLKLSSVTAADTAVYYCSSREYSSRWHFDYWG<br>QGTLVTVSS |
| 23203_2 VL<br>SEQ ID NO: 14 | DIQLTQSPSFLSASVGDRVTITCRASQGISSYLAWYQQKPGKAPKLLIYAASTLQ<br>SGVPSRFSGSGSGTEFTLTISSLQPEDFATYYCQQLNSYPLTFGGGTKVEIK |
| 23203_3 VH<br>SEQ ID NO: 23 | QVQLQQWGAGLLKPSETLSLTCTVSGGSFSGYYWTWIRQPPGKGLEWIGEINHAG<br>STNYNPSLKSRVTISVDTSKNQFSLKLSSVTAADTAVYYCSSREYSSRWHFDYWG<br>QGTLVTVSS |
| 23203_3 VL<br>SEQ ID NO: 24 | DIQLTQSPSFLSASVGDRVTITCRASQGISSYLAWYQQKPGKAPKLLIYAASTLQ<br>SGVPSRFSGSGSGTEFTLTISSLQPEDFATYYCQQLNSYPLTFGGGTKVEIK |
| 23203_4 VH<br>SEQ ID NO: 33 | QVQLQQWGAGLLKPSETLSLTCAVYGGSFSGYYWTWIRQPPGKGLEWIGEINHAG<br>STNYNPSLKSRVTISVDTSKNQFSLKLSSVTAADTAVYYCSSREYSSRWHFDYWG<br>QGTLVTVSS |
| 23203_4 VL<br>SEQ ID NO: 34 | DIQLTQSPSFLSASVGDRVTITCRASQGISSYLAWYQQKPGKAPKLLIYAASTLQ<br>SGVPSRFSGSGSGTEFTLTISSLQPEDFATYYCQQLNSYPLTFGGGTKVEIK |
| 22995 VH<br>SEQ ID NO: 43 | EVQLVESGGSLVQPGGSLRLSCAASGFTFSSSAMSWVRQAPGKGLEWVSTISGSD<br>SSTYDADSVKGRSTISRDNSKNTLYLQMNSLRADDTAVYYCAKKGAYCSGTICYD<br>PFDYWGQGTLVTVSS |
| 22995 VL<br>SEQ ID NO: 44 | DIVLTQSPVLAVSLGQRATISCRASQSVSISSINLMHWYQQKPGQQPKLLIYRAS<br>NLASGIPARFSGSGSGTDFTLTIDPVQADDIAAYYCQQSRESPLTFGGGTKVEIK |
| 22883 VH<br>SEQ ID NO: 53 | EVQLVESGGGLVQPGGSLRLSCAASGFTFSSYAMSWVRQAPGKGLEWVSAISGGG<br>DYTYYADSVKGRFTISRDNSKNTLYLQMNSLRAEDTAVYYCAKEEWELRGPFRYW<br>GQGTLVTVSS |
| 22883 VL<br>SEQ ID NO: 54 | DIQMTQSPSTLSASVGDRVTITCRASQSISSWLAWYQQKPGKAPKFLIYKASSLE<br>SGVPSRFSGSGSGTEFTLTISSLQPDDFATYYCQQYNGFSWTFGQGTKVEIK |

Table 3 shows heavy and light chain constant region amino acid sequences (CH and CL, respectively). "IgG$_1$-LALA" refers to the presence of "LALA" mutations in the heavy chain (L234A/L235A, numbered according to the Kabat numbering scheme) that are known to reduce effector function of the Fc region of IgG$_1$ antibodies (Hezareh et al., *J Virol.* 75(24):12161-68 (2001); Hessell et al., *Nature* 449(7158):101-04 (2007)).

TABLE 3

Constant region amino acid sequences of antibodies 23203_1, 23203_2, 23203_3, 23203_4, 22995, and 22883

| Fragment | Sequence (N-terminus to C-terminus) |
|---|---|
| IgG$_1$-LALA CH added to the VH SEQ ID NO: 61 | ASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKRVEPKSCDKT HTCPPCPAPEAAGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAVEWE SNGQPENNYKTTPPVLDSDGSFFLYSKLTVDKSRWQQGNVFSCSVMHEALHNH YTQKSLSLSPGK |
| Kappa CL added to the VL SEQ ID NO: 62 | RTVAAPSVFIFPPSDEQLKSGTASVVCLLNNFYPREAKVQWKVDNALQSGNSQ ESVTEQDSKDSTYSLSSTLTLSKADYEKHKVYACEVTHQGLSSPVTKSFNRGE C |

Table 4 shows heavy and light chain CDR amino acid sequences of antibodies 23203_1, 23203_2, 23203_3, 23203_4, 22995, and 22883, wherein the CDRs are defined according to the IMGT® system. SEQ ID NOs. of the sequences are shown in parentheses.

TABLE 4

CDR amino acid sequences of antibodies 23203_1, 23203_2, 23203_3, 23203_4, 22995, 22883

| | Sequence (N-terminus to C-terminus) | | | | | |
|---|---|---|---|---|---|---|
| Ab | H-CDR1 | H-CDR2 | H-CDR3 | L-CDR1 | L-CDR2 | L-CDR3 |
| 23203_1 | GGSFSGYY (5) | INHAGST (6) | CSSREYSSRWHFDYW (7) | QGISSY (8) | AAS (9) | CQQLNSYPLTF (10) |
| 23203_2 | GGSFSGYY (15) | INHSGST (16) | CSSREYSSRWHFDYW (17) | QGISSY (18) | AAS (19) | CQQLNSYPLTF (20) |
| 23203_3 | GGSFSGYY (25) | INHAGST (26) | CSSREYSSRWHFDYW (27) | QGISSY (28) | AAS (29) | CQQLNSYPLTF (30) |
| 23203_4 | GGSFSGYY (35) | INHAGST (36) | CSSREYSSRWHFDYW (37) | QGISSY (38) | AAS (39) | CQQLNSYPLTF (40) |
| 22995 | GFTFSSSA (45) | ISGSDSST (46) | CAKKGAYCSGTICYDPFDYW (47) | QSVSISSIN (48) | RAS (49) | CQQSRESPLTF (50) |
| 22883 | GFTFSSYA (55) | ISGGGDYT (56) | CAKEEWELRGPFRYW (57) | QSISSW (58) | KAS (59) | CQQYNGFSWTF (60) |

Table 5 shows SEQ ID NO information for antibodies 23203_1, 23203_2, 23203_3, 23203_4, 22995, and 22883. Unless otherwise stated, the sequences are amino acid sequences.

TABLE 5

SEQ ID NOs for antibodies 17303, 16040, 15833, 16154, 15888, and 15948

| Name | VH nt | VL nt | VH aa | VL aa | H-CDR1 | H-CDR2 | H-CDR3 | L-CDR1 | L-CDR2 | L-CDR3 |
|---|---|---|---|---|---|---|---|---|---|---|
| 23203_1 | 1 | 2 | 3 | 4 | 5 | 6 | 7 | 8 | 9 | 10 |
| 23203_2 | 11 | 12 | 13 | 14 | 15 | 16 | 17 | 18 | 19 | 20 |
| 23203_3 | 21 | 22 | 23 | 24 | 25 | 26 | 27 | 28 | 29 | 30 |
| 23203_4 | 31 | 32 | 33 | 34 | 35 | 36 | 37 | 38 | 39 | 40 |
| 22995 | 41 | 42 | 43 | 44 | 45 | 46 | 47 | 48 | 49 | 50 |
| 22883 | 51 | 52 | 53 | 54 | 55 | 56 | 57 | 58 | 59 | 60 | nt: nucleotide
aa: amino acid

Example 2: Measurement of Antibody Affinities Towards Human and Cynomolgus AXL This example demonstrates the binding of anti-AXL antibodies to recombinant human and cynomolgus AXL extracellular domains (ECDs) as measured by surface plasmon resonance (SPR).

Materials and Methods

The kinetic binding analysis was performed by surface plasmon resonance (SPR), using a Continuous Flow Microspotter (CFM, Wasatch Microfluidics, Salt Lake City, US) combined with an IBIS MX96 SPR instrument (IBIS Technologies, The Netherlands).

His-tagged human and cynomolgus AXL ECD were expressed in Expi293F cells and purified by Ni-NTA chromatography. Binding kinetics were measured under monovalent antigen conditions by immobilizing anti-AXL antibodies and keeping the monovalent AXL antigen in solution. Antibodies were captured onto a G-a-hu-IgG Fc SensEye® (Ssens BV, The Netherlands) for 15 minutes using a Continuous Flow Microspotter (CFM, Wasatch Microfluidics, Salt Lake City, US). After spotting, the SensEye® was positioned in the IBIS MX96 biosensor and captured proteins were fixed to the surface using FixIT kit (Ssens BV, The Netherlands). Kinetic analysis was performed by applying kinetic titration series (Karlsson et al., Anal Biochem. 349(1):136-47 (2006)), with antigen injections at increasing concentrations from 0.14 nM to 100 nM. Antigen association and dissociation was performed for 15 minutes. After each antigen injection series, the surface was regenerated by 100 mM $H_3PO_4$, pH 3 regeneration buffer. The recorded binding responses were fitted to a simple Langmuir 1:1 binding model with Scrubber 2 software for calculation of the on-rate ($k_{on}$ or ka), off-rate ($k_{off}$ or kd) and affinity ($K_D$) constants.

Results

The results of the affinity measurements demonstrate that antibodies 22995, 22883, and 23203 and versions thereof all bind human and cynomolgus AXL ECD with different affinities. The detailed binding kinetics are tabulated in Table 6 below.

TABLE 6

Binding kinetics of anti-AXL mAbs to human and cynomolgus AXL ECD as measured by SPR

| Antibody | AXL ECD | $k_{on}$ ($M^{-1}s^{-1}$) | $k_{off}$ ($s^{-1}$) | $K_D$ (M) |
|---|---|---|---|---|
| 22995 | Human | 8.2E+05 | 5.7E−04 | 6.9E−10 |
| 22995 | Cynomolgus | 1.4E+04 | 1.1E−03 | 8.0E−08 |
| 22883 | Human | 3.2E+04 | 3.1E−04 | 9.6E−09 |
| 22883 | Cynomolgus | 2.8E+04 | 2.0E−04 | 7.2E−09 |
| 23203_1 | Human | 1.4E+05 | 2.1E−03 | 1.5E−08 |
| 23203_1 | Cynomolgus | 1.8E+05 | 2.4E−03 | 1.3E−08 |
| 23203_2 | Human | 1.4E+05 | 1.6E−03 | 1.1E−08 |
| 23203_2 | Cynomolgus | 1.1E+05 | 1.6E−03 | 1.5E−08 |
| 23203_3 | Human | 1.1E+05 | 1.6E−03 | 1.5E−08 |
| 23203_3 | Cynomolgus | 1.4E+05 | 1.8E−03 | 1.3E−08 |
| 23203_4 | Human | 9.0E+04 | 2.3E−03 | 2.5E−08 |
| 23203_4 | Cynomolgus | 1.5E+05 | 2.1E−03 | 1.5E−08 |

Example 3: Cloning of Anti-AXL Reference Antibody Analogues

Table 7 shows information about the three anti-AXL antibodies used as references in the Examples. 10G5 analogue (BerGenBio) was produced in both $IgG_1$ and $IgG_1$-LALA, and thus is listed in two rows in the table.

Materials and Methods

The amino acid sequences encoding the heavy and light chain variable domains of the antibody analogues in Table 6 were obtained from the listed patents or patent applications. The protein sequences were reverse translated to DNA sequences with human codon usage. The corresponding DNA sequences were gene synthesized and cloned into expression vectors containing human heavy or light chain constant regions, resulting in expression of full-length antibody chains. The human antibody isotype selected for expression is listed in the antibody format column. CHO cells were transfected with the resulting expression plasmids using a standard protein expression system. The corresponding antibody supernatants were purified using standard protein A purification column chromatography.

TABLE 7

Listing of gene-synthesized antibody analogues
and the corresponding antibody format

| Antibody (Developer) | Antibody format | Source |
|---|---|---|
| Ax225 IgG$_1$-LALA analogue (Chugai) | IgG$_1$-LALA | U.S. Patent Publication 2015/9175091B2 (SEQ ID NOS: 3 and 7) |
| YW327.6S2 IgG$_1$-LALA analogue (Genentech) | IgG$_1$-LALA | U.S. Patent Publication 2014/8853369B2 (SEQ ID NOs: 103 and 104) |
| 10G5 analogue (BerGenBio) | IgG$_1$ | U.S. Patent Publication 2017/0349658A1 (SEQ ID NOS: 22 and 45) |
| 10G5 analogue (BerGenBio) | IgG$_1$-LALA | U.S. Patent Publication 2017/0349658A1 (SEQ ID NOS: 22 and 45) |

Example 4: In Vitro Binding of Anti-Human AXL Antibodies to CHO-S Cells Transiently Transfected with Human or Cynomolgus AXL Materials and Methods Six anti-human AXL antibodies and reference antibody analogues were evaluated by flow cytometry for in vitro binding to human or cynomolgus AXL extracellular domain transiently expressed on CHO-S cells. For comparison, reference antibody analogues were included in the evaluation. All antibodies were incubated in serial dilutions together with the transiently transfected CHO-S cells for 30 min at 4° C. Following two washing steps, the cells were incubated with AF647-conjugated secondary anti-human IgG (H+L) antibody for 30 min at 4° C. A final washing step was done prior to acquisition of the cells on an iQue Plus screener. Results were calculated by GrafPad Prism software.

Results

Figure 1B:
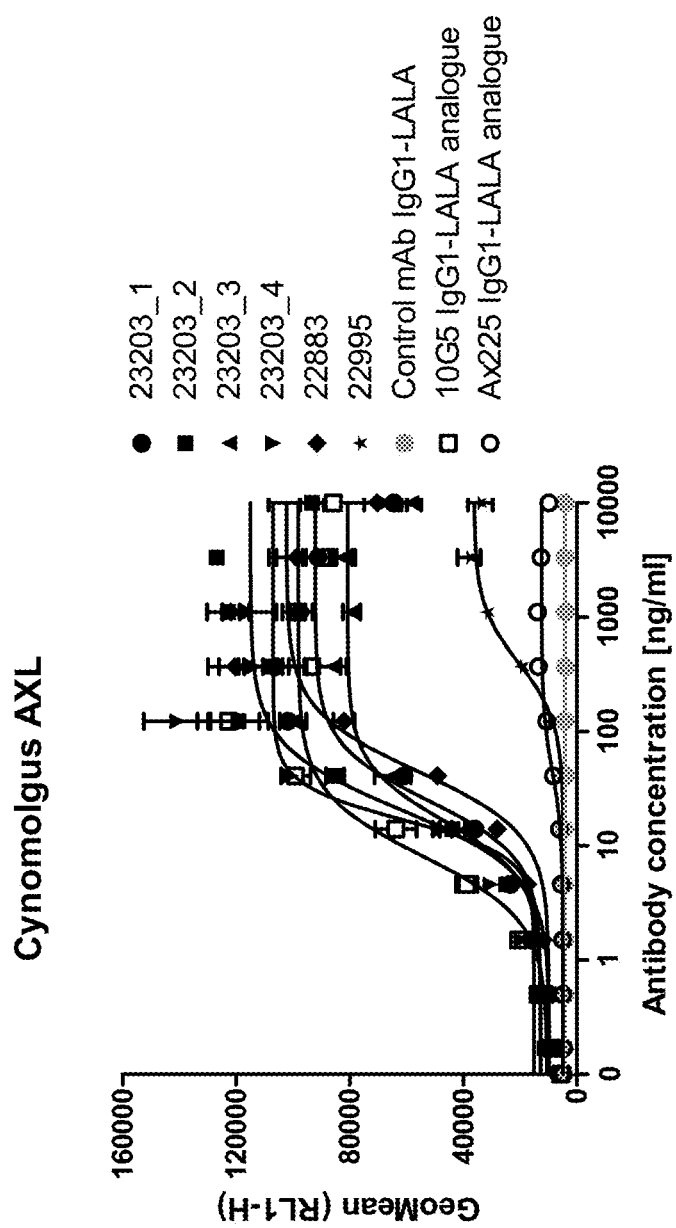
Figure 1C:
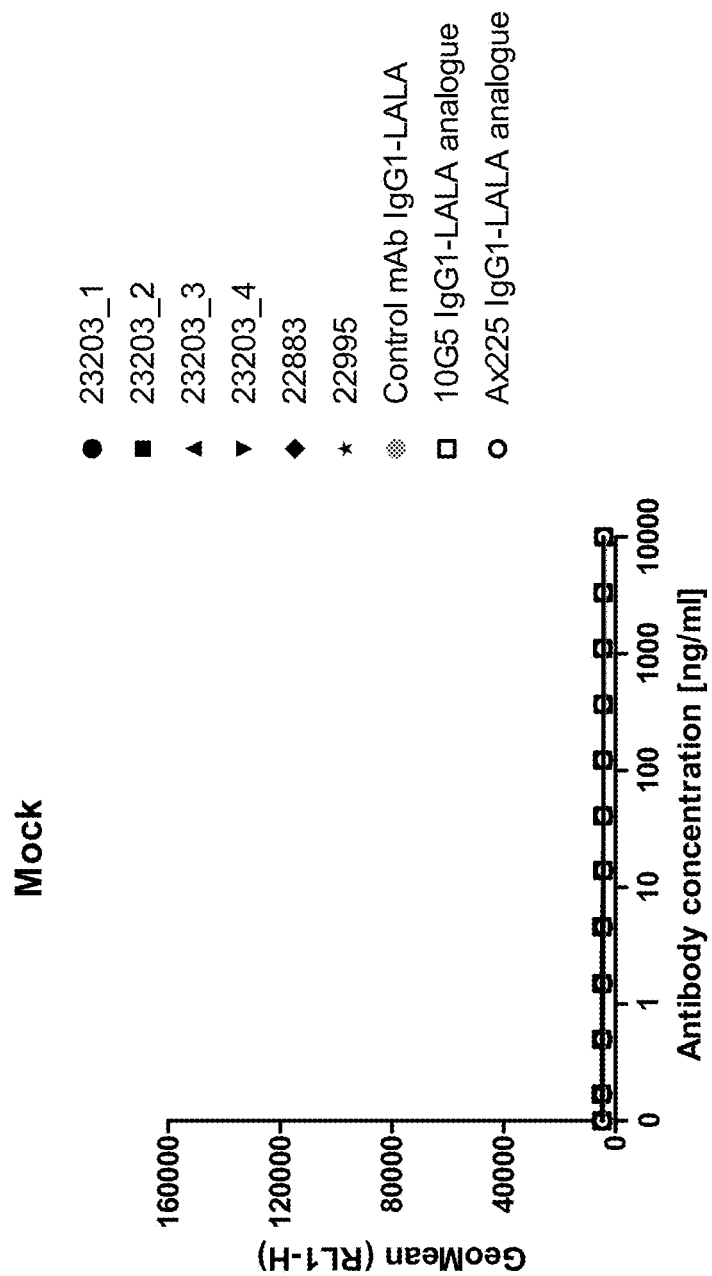

Dose-response curves of antibody binding to human or cynomolgus AXL ECD expressed on transiently transfected CHO-S cells are shown in FIGS. 1A-1C. All six anti-human AXL antibodies bind both human (FIG. 1A) and cynomolgus (FIG. 1B) AXL with varying potency and efficacy. Two reference antibodies are shown for comparison. None of the antibodies bind to mock transfected cells (FIG. 1C).

Example 5: In Vitro Functional Activity Screen of Anti-AXL Antibodies in an H1299 Proliferation Assay This example describes in vitro functional screening of a panel of anti-AXL monoclonal antibodies with the purpose of characterizing their functionality in the absence or presence of the GAS6 ligand. The antibodies were evaluated for their ability to inhibit GAS6 induced proliferation as well as for their agonistic activity in the absence of GAS6 in the AXL expressing H1299 cancer cell line. Reference antibody analogues were included for comparison.

Materials and Methods

Selected anti-AXL antibodies were evaluated in vitro for their ability to inhibit proliferation of the AXL expressing cancer cell line H1299. The H1299 cells were seeded at 2500 cells/well in a 384 well plate in RPMI 1640 Glutamax media supplemented with 2% FBS and 1% P/S and incubated for six days in a humidified incubator at 37° C. with antibodies at a concentration of up to 25 µg/mL, without GAS6 or in the presence of GAS6 (RnD Systems) at 1 µg/mL. Cell proliferation was quantified using WST-1 cell proliferation reagent (Roche) as per manufacturer's instructions. Several competitor analogues (Ax225 IgG$_1$-LALA analogue (Chugai), YW327.652 IgG$_1$-LALA analogue (Genentech) and 10G5 IgG$_1$-LALA analogue (BerGenBio)) were included for comparison.

Results

Figure 2:
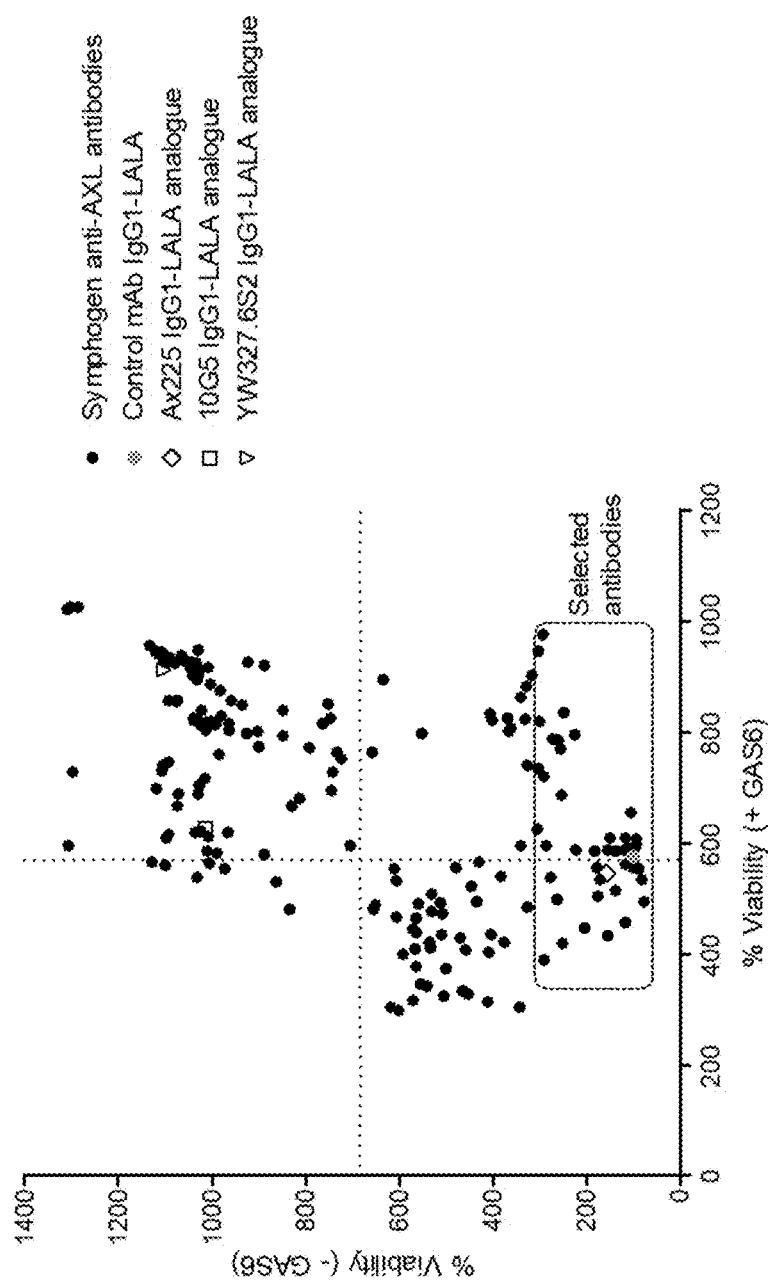
FIG. 2 is a graph showing the proliferation of H1299 cells after treatment with anti-AXL antibodies. Boxed antibodies were selected for further characterization. Data were normalized to untreated controls (no GAS6), with proliferative response in the presence of GAS6 on the X axis and proliferative response in the absence of GAS6 on the Y axis. Dotted horizontal and vertical lines signify proliferation levels upon GAS6 addition as compared to controls without GAS6, normalized for each setup (+ or − GAS6) separately. Each datapoint represents the mean of three technical replicates for each axis.

The results from the proliferation screen are shown in FIG. 2. It is apparent that the antibodies can be separated based on functional readout. Of the examined competitor analogues, 10G5 IgG$_1$-LALA (BerGenBio) and YW327.652 IgG$_1$-LALA (Genentech) displayed clear agonistic activity, while the Ax225 IgG$_1$-LALA (Chugai) displayed no activity either in the absence or presence of GAS6.

Antibodies showing no agonism in the absence of GAS6 were selected for further functional characterization, with emphasis on the rare antibodies with either pronounced counteraction or augmentation of GAS6-induced proliferation (indicated with stippled-line box in the figure).

Example 6: In Vitro Functional Activity of Anti-AXL Antibodies in an H1299 Proliferation Assay This example describes in vitro functional evaluation of six anti-AXL monoclonal antibodies with the purpose of demonstrating a dose-dependent antagonistic activity. The antibodies were evaluated for their ability to inhibit GAS6 induced proliferation as well as for their agonistic activity in the absence of GAS6 in the AXL-expressing H1299 cell line. Reference antibody analogues were included for comparison.

Materials and Methods

Selected anti-AXL antibodies were evaluated in further detail in vitro for their ability to induce proliferation of the AXL-expressing cancer cell line H1299. The H1299 cells were seeded in RPMI 1640 Glutamax media supplemented with 2% FBS and 1% P/S and incubated for six days with a two-fold titration of the indicated antibodies starting from 25 µg/mL, either without GAS6 or in the presence of GAS6 (RnD Systems) at 1 µg/mL. Cell proliferation was quantified using WST-1 cell proliferation reagent (Roche) as per manufacturer's instructions.

Results

Figure 3:
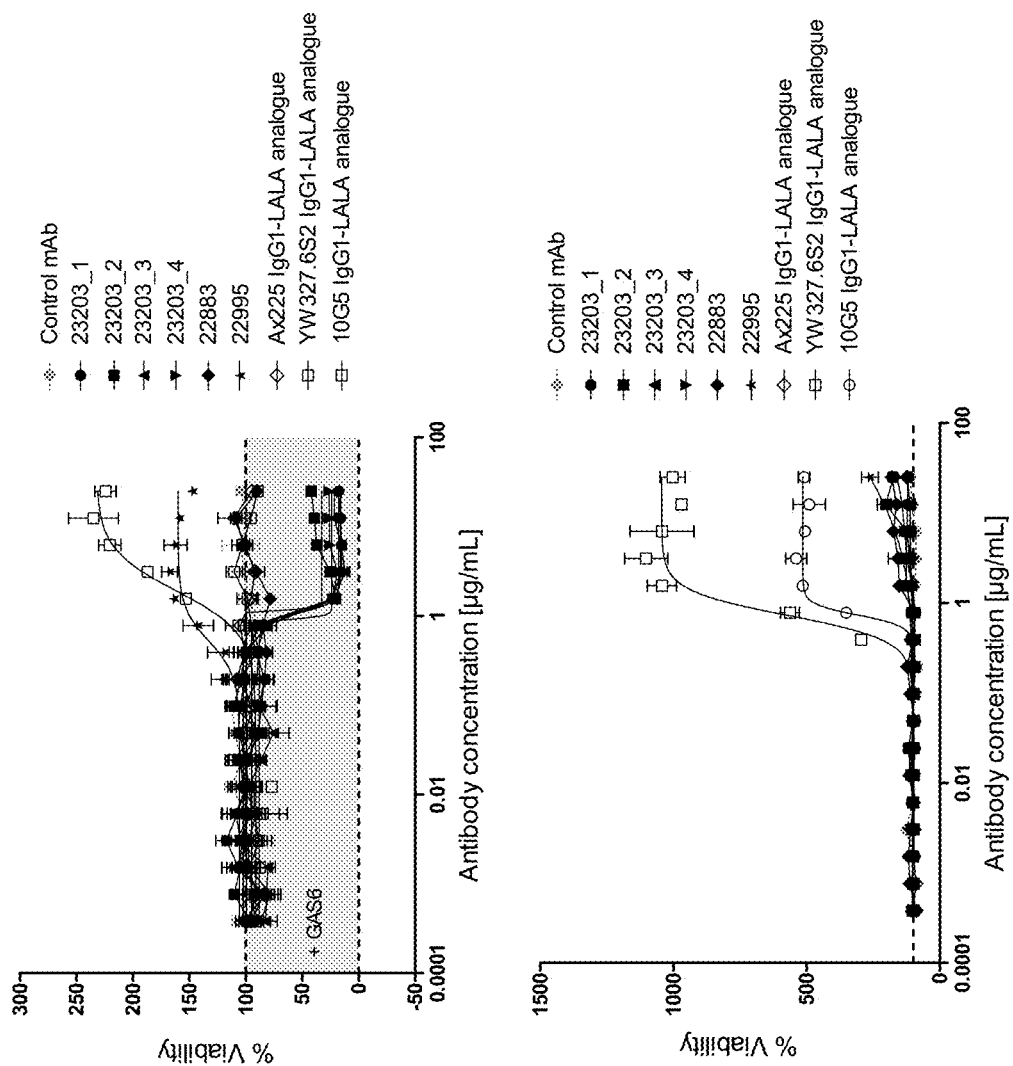
FIG. 3 is a pair of graphs showing the proliferation of H1299 cells treated with the indicated antibodies in the presence (upper panel) or absence (lower panel) of the ligand GAS6. Data are normalized to untreated control and each datapoint on the curves represents mean±SEM (n=3)

Six anti-AXL antibodies were evaluated for their ability to inhibit GAS6 induced proliferation of the AXL expressing H1299 cell line as well as for their agonistic activity in the absence of GAS6 (FIG. 3). Four of the antibodies (23203_1, 23203_2, 23203_3 and 23203_4) exhibited dose-dependent antagonistic activity as shown by their ability to efficiently block GAS6 induced proliferation of H1299 cells (top panel) and by their lack of agonistic activity in the absence of GAS6 (bottom panel). None of the other tested antibodies were able to block GAS6 induced proliferation (top panel). The YW327.652 IgG$_1$-LALA analogue and Ax225 IgG$_1$-LALA analogues were agonistic in the absence of GAS6 as shown by a strong induction of proliferation (bottom panel).

Example 7: In Vitro Functional Activity of Anti-AXL Antibodies in a Liposome Uptake Assay This example describes in vitro functional evaluation of six anti-AXL monoclonal antibodies with the purpose of demonstrating dose-dependent antagonistic activity.

Materials and Methods

Selected anti-AXL antibodies and reference antibody analogues were evaluated in further detail in vitro for their ability to inhibit GAS6 induced uptake of phosphatidylserine-containing liposomes in MDA-MB-468-AXL cells stably expressing exogenous AXL. Liposomes were prepared by mixing and hydrating molar ratios of the lipids POPC (1-palmitoyl-2-oleoyl-sn-glycero-3-phosphocholine, 43%), DOPS (1,2-dioleoyl-sn-glycero-3-phospho-L-serine (sodium salt); 11%), DOPE (1,2-dioleoyl-sn-glycero-3-phosphoethanolamine, 5%), cholesterol (40%), DOPE-NBD (1,2-dioleoyl-{12-[(7-nitro-2-1,3-benzoxadiazol-4-yl) amino]dodecanoyl}-sn-glycero-3-phosphoethanolamine, 1%) (Avanti Polar Lipids) followed by freeze/thaw cycles and extrusion through nucleopore filters (400 nm, Millipore) essentially as described (Ishimoto, *Biochem.* 127(3):411-7 (2000)). The MDA-MB-468-AXL cells were seeded in DMEM with 2% FBS and 1% P/S one day prior to the assay. On the next day, GAS6 (R&D systems, 1 µg/mL), liposomes (25 µM), anti-AXL antibodies, and reference antibodies as well as control antibodies were added to the cells. The antibodies were titrated 4-fold from 6 µg/mL. Uptake was measured and analyzed using the IncuCyte automated microscope platform.

Results

Figure 4:
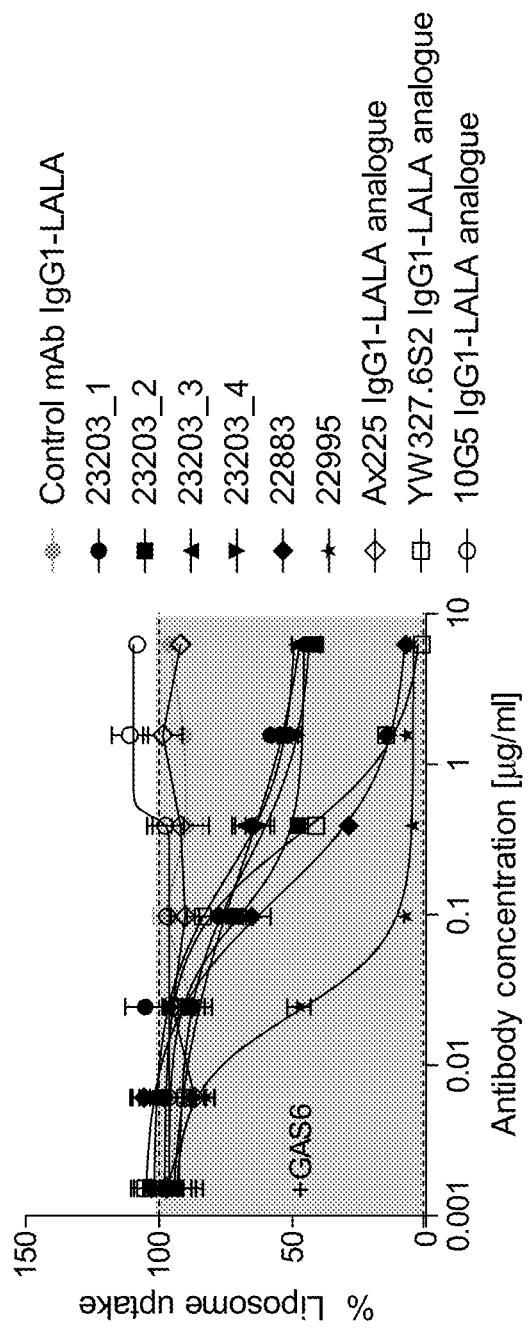
FIG. 4 is a graph showing the GAS6-induced uptake of liposomes by MDA-MB-468-AXL cells treated with the indicated antibodies. Data are normalized to GAS6-treated controls (dotted line) and presented as mean±SEM. Each datapoint represents the mean of three technical replicates.

The results from the liposome uptake assay are shown in FIG. 4. It is evident that the inhibitory function of the anti-AXL antibodies is concentration dependent and that all antibodies are inhibiting GAS6-induced uptake of phosphatidylserine containing liposomes, albeit with varying potency and efficacy. The YW327.6S2 IgG$_1$-LALA (Genentech) analogue shows antagonistic activity, while the Ax225 IgG$_1$-LALA (Chugai) and the 10G5 IgG$_1$-LALA (BerGenBio) analogues show no functionality.

Example 8: In Vivo Efficacy of Anti-AXL Antibodies in a Xenogeneic Tumor Model

This example demonstrates the in vivo efficacy of antibodies 22995 and 23203_2 in a xenogeneic tumor model.

Materials and Methods

1×10$^7$ MDA-MB-231 human breast cancer cells were inoculated subcutaneously together with Matrigel into the flanks of 6-8 week old female NOD.Scid mice. Tumors were measured three times weekly by caliper in two dimensions and tumor volume in mm$^3$ was calculated according to the formula: (width)$^2$×length×0.5. At an average tumor size of 40 mm$^3$, the mice were randomized and treatment initiated. The mice were treated three times weekly with a total of six treatments by intraperitoneal injection of vehicle buffer or either one of the two monoclonal antibodies 22995 or 23203_2 followed by an observation period. The antibody treatments were dosed at 10 mg/kg or 50 mg/kg. Two-way ANOVA with Bonferroni's multiple comparisons test was applied to compare tumor volumes at each time-point between treatment groups. Statistical analyses were performed using GraphPad Prism version 5.0 (GraphPad Software, Inc.).

Results

Figure 5A:
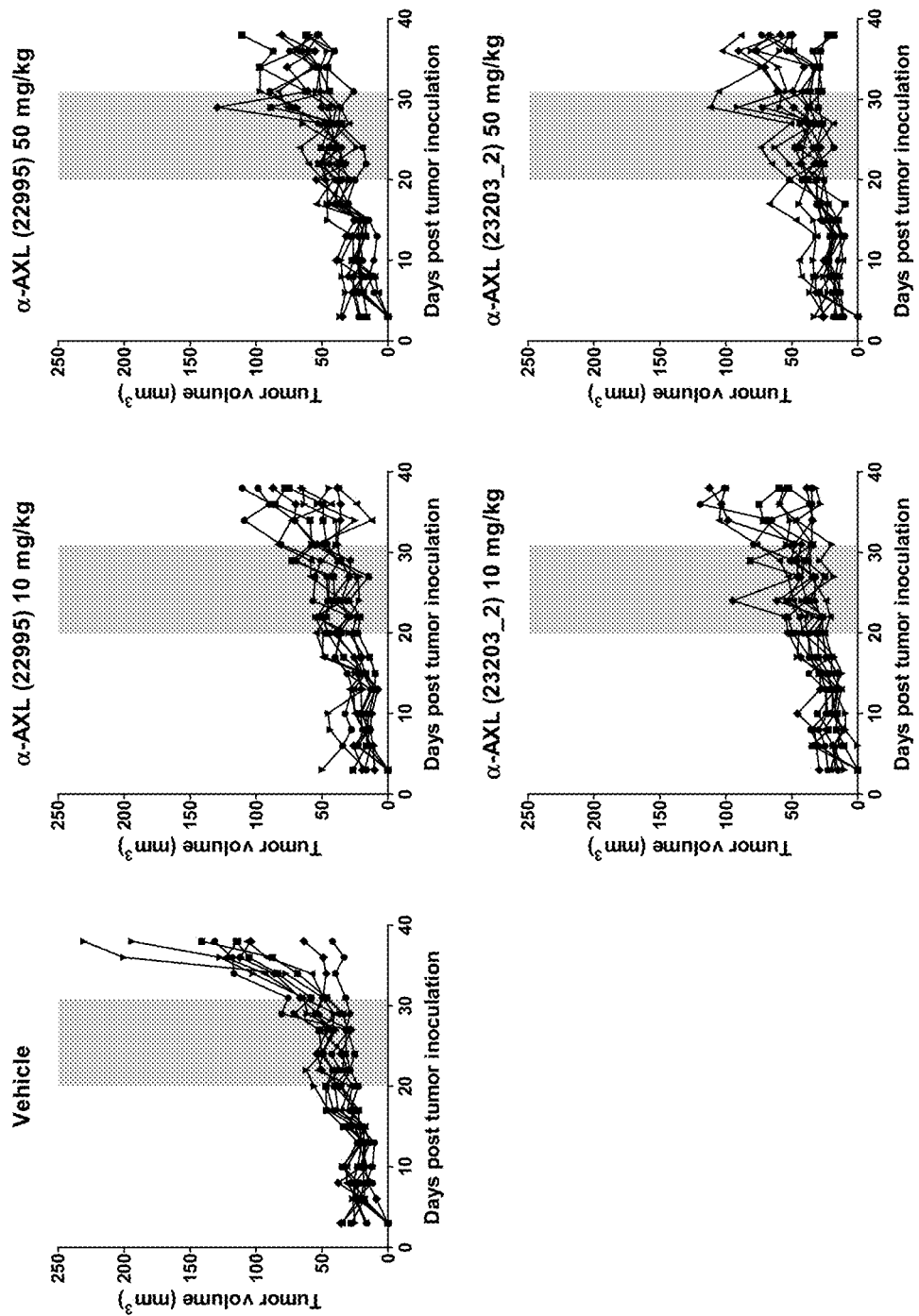
FIGS. 5A and 5B are a pair of graphs showing the effect of two AXL antibodies (22995 and 23203_2) or vehicle treatment on tumor growth in NOD.Scid mice engrafted with human breast cancer MDA-MB-231 cells. The grey area denotes the treatment period. Data are presented as mean±SEM. ****P<0.0001.
Figure 5B:
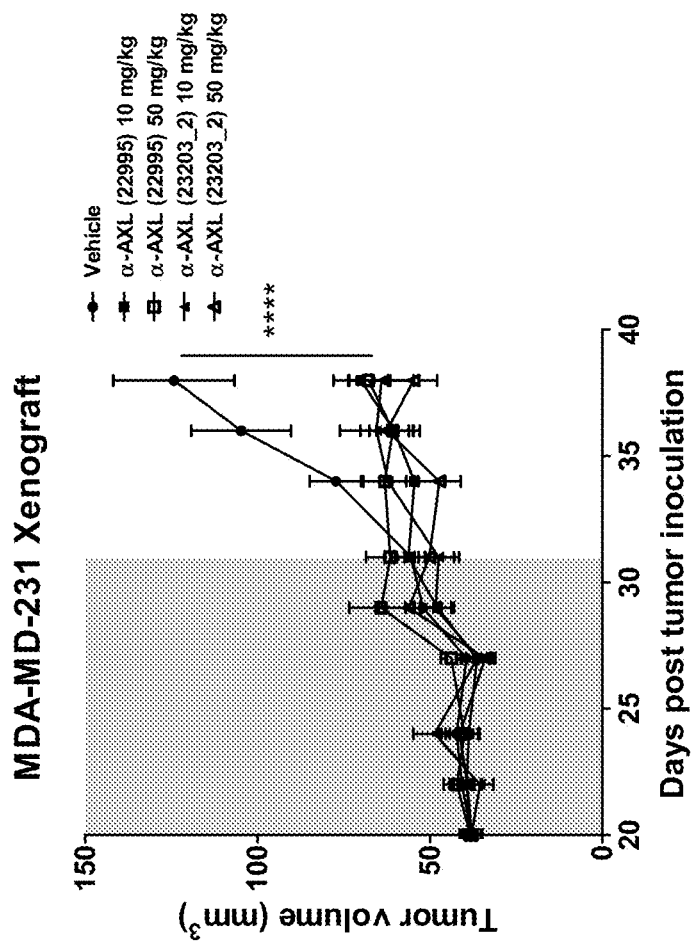

On day 20 post-inoculation, at an average tumor size of 40 mm$^3$, the mice were randomized into five groups of ten animals and treatment was initiated. The results showed a profound tumor inhibitory effect of both monoclonal antibodies against AXL (22995 and 23203_2) in the tested tumor model (**$P<0.0001$) (FIGS. 5A and 5B**).

Example 9: Epitope Binning of Anti-AXL Antibodies

This example describes cross-competition analysis of anti-AXL antibodies 23203-1, 22995, and 22883, and 10G5 and YW327.652 IgG1-LALA analogues, as measured by Surface Plasmon Resonance (SPR). Non-blocking relationships between the antibodies indicate that they recognize different epitopes of AXL.

Materials and Methods

Investigation of paired antibody competition was performed by SPR using an IBIS-MX96 instrument (IBIS, Netherlands). Anti-AXL antibodies were spotted onto a G-a-hu-IgG Fc SensEye® by capturing for 15 minutes using a Continuous Flow Microspotter, followed by blocking of residual binding sites by Herceptin (trastuzumab) and chemical cross-linking by SensEye FixIt kit (IBIS, Netherlands). After sensor preparation, antibody competition analysis was performed using a classical sandwich assay. Recombinant AXL-His ECD antigen was injected at a 100 nM concentration and captured by the conjugated array of anti-AXL antibodies. Next, individual injections of each of the AXL antibodies diluted to 100 nM in running buffer were performed to establish antibody competition patterns. Recombinant AXL ligand, GAS6 (100 nM), was included as an analyte to characterize ligand blocking antibodies. Data were analyzed by Epitope Binning 2.0 (Wasatch, USA).

Results

FIG. 6 shows normalized values for the binding of the indicated antibodies or the AXL ligand, GAS6, to AXL ECD prebound to an array of immobilized anti-AXL antibodies on the biosensor surface. Immobilized antibodies are represented as rows and antibodies in solution as columns. Non-blocking (sandwiching) antibodies are shown as white and blocking antibodies are shown as grey.

The 10G5 and YW327.6S2 analogues, tested in both directions, were self-blocking. All of the tested antibodies blocked GAS6 except a control antibody known not to block the ligand. None of tested antibodies 22995, 23203-1, and 22883 competed with the YW327.6S2 IgG1-LALA analogue, and only one antibody, 22883, competed with the 10G5 analogue.

In conclusion, the data show that antibodies 22995 and 23203-1 recognize different epitopes on the AXL ECD than the 10G5 and YW327.6S2 IgG1-LALA analogues.

Example 10: Anti-AXL Antibody Binding to Chimeric AXL Domain Mutants

This example describes the binding of anti-AXL antibodies to recombinant chimeric AXL ECD, where domains of the mouse AXL sequence were exchanged for human AXL sequence. Binding of the anti-AXL antibodies to the chimeric proteins was measured by Biolayer Interferometry (BLI) to determine the AXL domains bound by antibodies 23203-1, 22995, the 10G5 analogue, and the YW327.6S2 IgG1-LALA analogue.

Materials and Methods

The protein sequences of human and mouse AXL were downloaded from UniProt (Accession Nos. P30530 and Q80YQ3, respectively). Chimeric proteins were generated by substituting Ig1-2 and Fn-1-2 in the mouse AXL ECD with the human counterparts as indicated in FIG. 7. His-tagged wild type and mutated human AXL constructs were generated by standard gene synthesis techniques, and proteins were expressed transiently using an ExpiCHO™ expression system. Antibody binding to captured chimeric proteins was measured by BLI using an Octet QK384 instrument. His-tagged chimeric proteins were captured from supernatant by pre-equilibrated Anti-Penta-HIS (HIS1K) Biosensors (Sartorius) for 10 min. Association of anti-AXL antibodies was measured for 10 min at saturating conditions. Sensors were regenerated in 10 mM glycine pH 1.5 for 5 s×3. Data were analyzed in ForteBio Data Analysis 8.2 by subtracting reference surface levels and responses were quantified at the end of antibody association.

Results

FIG. 7 shows normalized responses (nm) of binding of the indicated antibodies to captured chimeric human/mouse AXL ECD proteins.

All antibodies bound full-length human AXL ECD (HuAxl_ECD) consisting of two immunoglobulin-like (Ig1 and Ig2) domains followed by two fibronectin type 3-like domains (Fn1 and Fn2). The YW327.6S2 analogue is cross-reactive with murine AXL and bound all chimeric proteins, demonstrating that the protein constructs were generally functional (Ye et al., *Oncogene* 29:5254-5264 (2010)). Antibody 22995 and the 10G5 analogue both bound to the Ig1 domain of AXL, while antibody 23203-1 bound to the Ig2 domain.

The invention claimed is:

1. An anti-AXL antibody or an antigen-binding portion thereof, wherein said antibody comprises the H-CDR1-3 and L-CDR1-3 amino acid sequences of:
   a) SEQ ID NOs: 45-50, respectively;
   b) SEQ ID NOs: 15-20, respectively;
   c) SEQ ID NOs: 5-10, respectively;
   d) SEQ ID NOs: 25-30, respectively;
   e) SEQ ID NOs: 35-40, respectively; or
   f) SEQ ID NOs: 55-60, respectively.

2. The anti-AXL antibody or antigen-binding portion of claim 1, wherein said antibody comprises a heavy chain variable domain amino acid sequence and a light chain variable domain amino acid sequence that are at least 90% identical to the amino acid sequences of:
   a) SEQ ID NOs: 43 and 44, respectively;
   b) SEQ ID NOs: 13 and 14, respectively;
   c) SEQ ID NOs: 3 and 4, respectively;
   d) SEQ ID NOs: 23 and 24, respectively;
   e) SEQ ID NOs: 33 and 34, respectively; or
   f) SEQ ID NOs: 53 and 54, respectively.

3. The anti-AXL antibody or antigen-binding portion of claim 1, wherein said antibody comprises a heavy chain variable domain and a light chain variable domain comprising the amino acid sequences of:
   a) SEQ ID NOs: 43 and 44, respectively;
   b) SEQ ID NOs: 13 and 14, respectively;
   c) SEQ ID NOs: 3 and 4, respectively;
   d) SEQ ID NOs: 23 and 24, respectively;
   e) SEQ ID NOs: 33 and 34, respectively; or
   f) SEQ ID NOs: 53 and 54, respectively.

4. The anti-AXL antibody of claim 1, wherein the antibody is of isotype subtype $IgG_1$.

5. The anti-AXL antibody of claim 1, wherein the antibody is of isotype subtype $IgG_1$ and comprises a mutation from Leu to Ala in either or both of heavy chain amino acid positions 234 and 235, which are numbered according to the Eu numbering scheme.

6. An anti-AXL antibody that comprises:
   a) a heavy chain (HC) comprising the amino acid sequences of SEQ ID NOs: 43 and 61 and a light chain (LC) comprising the amino acid sequences of SEQ ID NOs: 44 and 62;
   b) an HC comprising the amino acid sequences of SEQ ID NOs: 13 and 61 and an LC comprising the amino acid sequences of SEQ ID NOs: 14 and 62;
   c) an HC comprising the amino acid sequences of SEQ ID NOs: 3 and 61 and an LC comprising the amino acid sequences of SEQ ID NOs: 4 and 62;

d) an HC comprising the amino acid sequences of SEQ ID NOs: 23 and 61 and an LC comprising the amino acid sequences of SEQ ID NOs: 24 and 62;
e) an HC comprising the amino acid sequences of SEQ ID NOs: 33 and 61 and an LC comprising the amino acid sequences of SEQ ID NOs: 34 and 62; or
f) an HC comprising the amino acid sequences of SEQ ID NOs: 53 and 61 and an LC comprising the amino acid sequences of SEQ ID NOs: 54 and 62.

7. The anti-AXL antibody or antigen-binding portion of claim 1, wherein the antibody or antigen-binding portion has at least one property selected from:
   a) binds to human AXL with a $K_D$ of $3 \times 10^{-8}$ M or less;
   b) binds to cynomolgus AXL with a $K_D$ of $8 \times 10^{-8}$ M or less;
   c) does not bind to mouse AXL;
   d) binds to the Ig1 or Ig2 domain of human AXL;
   e) inhibits binding of GAS6 to human AXL;
   f) inhibits proliferation of H1299 cells in vitro in the presence of GAS6;
   g) does not exhibit agonistic activity in the absence of GAS6;
   h) inhibits GAS6-induced uptake of phosphatidylserine-containing liposomes in MDA-MB-468-AXL cells stably expressing exogenous AXL; and
   i) inhibits tumor growth in vivo.

8. A pharmaceutical composition comprising an anti-AXL antibody or antigen-binding portion of claim 1 and a pharmaceutically acceptable excipient.

9. The pharmaceutical composition of claim 8, further comprising an immunostimulatory agent, a vaccine, a chemotherapeutic agent, an anti-neoplastic agent, an anti-angiogenic agent, or a tyrosine kinase inhibitor.

10. Isolated nucleic acid molecule(s) comprising a nucleotide sequence that encodes the heavy chain sequence, and a nucleotide sequence that encodes the light chain sequence, of the anti-AXL antibody of claim 1.

11. The isolated nucleic acid molecule(s) of claim 10, comprising the nucleotide sequence of any one of SEQ ID NOs: 41, 42, 11, 12, 1, 2, 21, 22, 31, 32, 51, and 52.

12. Vector(s) comprising the isolated nucleic acid molecule(s) of claim 10, wherein said vectors further comprise expression control sequences operably linked to the nucleotide sequences.

13. A host cell comprising a nucleotide sequence that encodes the heavy chain sequence, and a nucleotide sequence that encodes the light chain sequence, of the anti-AXL antibody or antigen-binding portion of claim 1.

14. A method for producing an anti-AXL antibody or an antigen-binding portion thereof, comprising providing a host cell of claim 13, culturing said host cell under conditions suitable for expression of the antibody or portion, and isolating the resulting antibody or portion.

15. A bi-specific binding molecule comprising the antigen-binding portion of an anti-AXL antibody of claim 1 and the antigen-binding portion of another, distinct antibody.

16. A method for treating cancer in a human patient, comprising administering to said patient a therapeutically effective amount of the anti-AXL antibody or antigen-binding portion of claim 1.

17. The method of claim 16, wherein the cancer is in a tissue selected from the group consisting of skin, lung, intestine, colon, ovary, brain, prostate, kidney, soft tissues, the hematopoietic system, head and neck, liver, bone, bladder, breast, stomach, uterus, cervix, and pancreas.

18. The method of claim 16, wherein the cancer is melanoma, head and neck cancer, glioblastoma, thyroid cancer, non-small cell lung cancer, breast cancer, pancreatic cancer, ovarian cancer, cervical cancer, fallopian tube carcinoma, primary peritoneal carcinoma, endometrial cancer, urothelial carcinoma, renal cell carcinoma, colorectal cancer, rectal cancer, prostate cancer, mesothelioma, squamous cell carcinoma, sarcoma, chronic myeloid leukemia, acute myeloid leukemia, chronic lymphocytic leukemia, small lymphocytic leukemia, myelodysplastic syndrome, or Hodgkin's lymphoma.

19. The method of claim 16, further comprising administering to the patient an immunostimulatory agent, a vaccine, a chemotherapeutic agent, an anti-neoplastic agent, an anti-angiogenic agent, a tyrosine kinase inhibitor, or radiation therapy.

* * * * *

SEQUENCE LISTING

```
<160> NUMBER OF SEQ ID NOS: 67

<210> SEQ ID NO 1
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tgcaggagtc tggccctggc ctggtgaagc caagcgagac actgtctctg      60
acctgtaccg tgtctggcgg ctcttttct ggatattact ggagctggat cagacagcca     120
cccggcaagg gcctggagtg gatcggcgag atcaaccacg ctggctccac caattacaac     180
ccctctctga agagcagagt gaccatctct gtggatacct ccaagaacca gttctccctg     240
aagctgtcta gcgtgacagc cgctgataca gccgtgtact attgctcttc ccgcgagtac     300
tcctctcgtt ggcacttcga ctactgggc cagggcacac tggtgaccgt ctcgagt       357

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
gatatccagc tgacccagtc ccctagcttc ctgtctgctt ccgtgggcga tagagtgacc      60
atcacatgta gagcctctca gggcatctcc tcttacctgg cttggtatca gcagaagcct     120
ggcaaggctc ctaagctgct gatctatgct gcctctacac tgcagtctgg cgtgccatcc     180
cggttcagcg gctctggcag cggcaccgag ttcacactga ccatctcctc tctgcagcca     240
gaggatttcg ctacctacta ttgccagcag ctgaacagct accctctgac atttggcggc     300
ggcacaaagg tggagatcaa g                                              321

<210> SEQ ID NO 3
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
```

-continued

```
                 50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ser
                 85                  90                  95

Ser Arg Glu Tyr Ser Ser Arg Trp His Phe Asp Tyr Trp Gly Gln Gly
            100                 105                 110

Thr Leu Val Thr Val Ser Ser
        115

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Leu Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
             20                  25                  30

Leu Ala Trp Tyr Gln Gln Lys Pro Gly Lys Ala Pro Lys Leu Leu Ile
         35                  40                  45

Tyr Ala Ala Ser Thr Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
            100                 105

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Gly Ser Phe Ser Gly Tyr Tyr
 1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Asn His Ala Gly Ser Thr
 1               5

<210> SEQ ID NO 7
<211> LENGTH: 15
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 7

Cys Ser Ser Arg Glu Tyr Ser Ser Arg Trp His Phe Asp Tyr Trp
1               5                   10                  15

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gly Ile Ser Ser Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Ser
1

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Gln Gln Leu Asn Ser Tyr Pro Leu Thr Phe
1               5                   10

<210> SEQ ID NO 11
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
caggtgcagc tgcagcagtg gggcgctggc ctgctgaagc cttctgagac actgtctctg      60
acctgtgccg tgtatggcgg ctcttttttcg ggctattact ggacctggat cagacagcct    120
ccaggcaagg gcctggagtg gatcggcgag atcaatcact ccggctctac caactacaat    180
ccatccctga agagcagagt gaccatctcc gtggatacct ccaagaatca gttttctctg    240
aagctgtcct ctgtgacagc tgctgatacc gccgtgtact attgctctag cagagagtac    300
tcctctagat ggcacttcga ttactggggc cagggcacac tggtgaccgt ctcgagt       357

<210> SEQ ID NO 12
<211> LENGTH: 321
<212> TYPE: DNA
<213> ORGANISM: Artificial Sequence
```

```
<220> FEATURE:
<223> OTHER INFORMATION: Description of Artificial Sequence: Synthetic
      polynucleotide

<400> SEQUENCE: 12
gatatccagc tgacccagtc ccctagcttc ctgtctgctt ccgtgggcga tagagtgacc        60
atcacatgta gagcctctca gggcatctcc tcttacctgg cttggtatca gcagaagcct       120
ggcaaggctc ctaagctgct gatctatgct gcctctacac tgcagtctgg cgtgccatcc       180
cggttcagcg gctctggcag cggcaccgag ttcacactga ccatctcctc tctgcagcca       240
gaggatttcg ctacctacta ttgccagcag ctgaacagct accctctgac atttggcggc       300
ggcacaaagg tggagatcaa g                                                 321

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Ser Arg Glu Tyr Ser Ser Arg Trp His Phe Asp Tyr Trp Gly Gln Gly
            100                 105                 110

Thr Leu Val Thr Val Ser Ser
        115

<210> SEQ ID NO 14
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Phe Ser Gly Tyr Tyr
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Asn His Ser Gly Ser Thr
1               5

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ser Ser Arg Glu Tyr Ser Ser Arg Trp His Phe Asp Tyr Trp
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Gly Ile Ser Ser Tyr
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ala Ser
1

<210> SEQ ID NO 20
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Cys Gln Gln Leu Asn Ser Tyr Pro Leu Thr Phe
1               5                   10

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caggtgcagc tgcagcagtg gggcgctggc ctgctgaagc cttctgagac actgtctctg    60
acctgtaccg tgtctggcgg ctcttttttcc ggctattact ggacctggat caggcagcca   120
cctggcaagg gcctggagtg gatcggcgag atcaaccacg ctggctccac caactacaat   180
ccttccctga gtctagagt gaccatctcc gtggatacct ccaagaacca gttctccctg   240
aagctgtcct ctgtgaccgc cgctgataca gccgtgtact attgctccag cagagagtac   300
tcctctagat ggcacttcga ctactggggc cagggcacac tggtgacagt ctcgagt     357

<210> SEQ ID NO 22
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gatatccagc tgacccagtc ccctagcttc ctgtctgctt ccgtgggcga tagagtgacc    60
atcacatgta gagcctctca gggcatctcc tcttacctgg cttggtatca gcagaagcct   120
ggcaaggctc ctaagctgct gatctatgct gcctctacac tgcagtctgg cgtgccatcc   180
cggttcagcg gctctggcag cggcaccgag ttcacactga ccatctcctc tctgcagcca   240
gaggatttcg ctacctacta ttgccagcag ctgaacagct accctctgac atttggcggc   300
ggcacaaagg tggagatcaa g                                            321

<210> SEQ ID NO 23
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Gln Leu Gln Gln Trp Gly Ala Gly Leu Leu Lys Pro Ser Glu
1               5                   10                  15

Thr Leu Ser Leu Thr Cys Thr Val Ser Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60
```

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Ser Arg Glu Tyr Ser Ser Arg Trp His Phe Asp Tyr Trp Gly Gln Gly
            100                 105                 110

Thr Leu Val Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys
            100                 105

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Phe Ser Gly Tyr Tyr
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asn His Ala Gly Ser Thr
1               5

<210> SEQ ID NO 27
<211> LENGTH: 15
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 27

Cys Ser Ser Arg Glu Tyr Ser Ser Arg Trp His Phe Asp Tyr Trp
1               5                   10                  15

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Gly Ile Ser Ser Tyr
1               5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Ala Ser
1

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Gln Gln Leu Asn Ser Tyr Pro Leu Thr Phe
1               5                   10

<210> SEQ ID NO 31
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caggtgcagc tgcagcagtg gggcgctggc ctgctgaagc cttctgagac actgtctctg      60
acctgtgccg tgtatggcgg ctcttttttcc ggctattact ggacctggat caggcagcca    120
cctggcaagg gcctggagtg gatcggcgag atcaaccacg ctggctccac caactacaat    180
ccttccctga agtctagagt gaccatctcc gtggatacct ccaagaacca gttctccctg    240
aagctgtcct ctgtgaccgc cgctgataca gccgtgtact attgctccag cagagagtac    300
tcctctagat ggcacttcga ctactggggc cagggcacac tggtgacagt ctcgagt       357

<210> SEQ ID NO 32
<211> LENGTH: 321
<212> TYPE: DNA
<213> ORGANISM: Artificial Sequence
<220> FEATURE:

<223> OTHER INFORMATION: Description of Artificial Sequence: Synthetic
    polynucleotide

<400> SEQUENCE: 32
gatatccagc tgacccagtc ccctagcttc ctgtctgctt ccgtgggcga tagagtgacc    60
atcacatgta gagcctctca gggcatctcc tcttacctgg cttggtatca gcagaagcct    120
ggcaaggctc ctaagctgct gatctatgct gcctctacac tgcagtctgg cgtgccatcc    180
cggttcagcg gctctggcag cggcaccgag ttcacactga ccatctcctc tctgcagcca    240
gaggatttcg ctacctacta ttgccagcag ctgaacagct accctctgac atttggcggc    300
ggcacaaagg tggagatcaa g    321

<210> SEQ ID NO 33
<211> LENGTH: 119
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 33

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Thr Trp Ile Arg Gln Pro Pro Gly Lys Gly Leu Glu Trp Ile
        35                  40                  45

Gly Glu Ile Asn His Ala Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ser
                85                  90                  95

Ser Arg Glu Tyr Ser Ser Arg Trp His Phe Asp Tyr Trp Gly Gln Gly
            100                 105                 110

Thr Leu Val Thr Val Ser Ser
        115

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 34

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu

```
                    85                  90                  95
Thr Phe Gly Gly Gly Thr Lys Val Glu Ile Lys
            100                 105
```

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Gly Gly Ser Phe Ser Gly Tyr Tyr
1               5
```

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ile Asn His Ala Gly Ser Thr
1               5
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Cys Ser Ser Arg Glu Tyr Ser Ser Arg Trp His Phe Asp Tyr Trp
1               5                   10                  15
```

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gln Gly Ile Ser Ser Tyr
1               5
```

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Ala Ala Ser
1
```

<210> SEQ ID NO 40
<211> LENGTH: 11
<212> TYPE: PRT

-continued

<213> ORGANISM: Artificial Sequence
<220> FEATURE:
<223> OTHER INFORMATION: Description of Artificial Sequence: Synthetic
      peptide

<400> SEQUENCE: 40

Cys Gln Gln Leu Asn Ser Tyr Pro Leu Thr Phe
1               5                   10

<210> SEQ ID NO 41
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaggtgcagc tggtggagtc tggcggcagc ctggtgcagc ccggcggctc tctgagactg      60
tcttgtgccg cttctggctt taccttctct tcatccgcta tgtcttgggt gcgccaagcc     120
ccaggcaagg gcctggagtg ggtgtctacc atctccggca cgattcttc cacctacgac      180 gctgattccg tgaagggcag aagcacaatc tccagggaca attccaagaa cacccctgtat   240 ctgcagatga actccctgag agctgatgac accgccgtgt attactgcgc taagaagggc     300
gcttattgtt ccggcacaat ctgctacgat cccttcgact attggggcca gggcacactg     360
gtgaccgtct cgagt                                                      375

<210> SEQ ID NO 42
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gatatcgtgc tgacccagtc tccagtgctg gccgtgtccc tgggccagag agctaccatc      60
tcttgcagag cttctcagtc cgtgtctatc agctccatca acctgatgca ttggtaccag     120
cagaagccag gccagcagcc aaagctgctg atctacagag ccagcaacct ggcttctggc     180
atcccagcta gattctccgg ctctggcagc ggcacagatt tcaccctgac aatcgatcct     240
gtgcaggctg acgatatcgc cgcttattac tgccagcagt tccagagagtc tcctctgacc     300 tttggcggcg gcacaaaggt ggagatcaag                                      330

<210> SEQ ID NO 43
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Ser Leu Val Gln Pro Gly Gly
1               5                   10                  15

Ser Leu Arg Leu Ser Cys Ala Ala Ser Gly Phe Thr Phe Ser Ser Ser
            20                  25                  30

Ala Met Ser Trp Val Arg Gln Ala Pro Gly Lys Gly Leu Glu Trp Val
        35                  40                  45

Ser Thr Ile Ser Gly Ser Asp Ser Ser Thr Tyr Asp Ala Asp Ser Val

```
            50                  55                  60
Lys Gly Arg Ser Thr Ile Ser Arg Asp Asn Ser Lys Asn Thr Leu Tyr
 65                  70                  75                  80

Leu Gln Met Asn Ser Leu Arg Ala Asp Thr Ala Val Tyr Tyr Cys
                 85                  90                  95

Ala Lys Lys Gly Ala Tyr Cys Ser Gly Thr Ile Cys Tyr Asp Pro Phe
                100                 105                 110

Asp Tyr Trp Gly Gln Gly Thr Leu Val Thr Val Ser Ser
                115                 120                 125

<210> SEQ ID NO 44
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Leu Thr Gln Ser Pro Val Leu Ala Val Ser Leu Gly Gln
  1               5                  10                  15

Arg Ala Thr Ile Ser Cys Arg Ala Ser Gln Ser Val Ser Ile Ser Ser
                 20                  25                  30

Ile Asn Leu Met His Trp Tyr Gln Gln Lys Pro Gly Gln Gln Pro Lys
                 35                  40                  45

Leu Leu Ile Tyr Arg Ala Ser Asn Leu Ala Ser Gly Ile Pro Ala Arg
             50                  55                  60

Phe Ser Gly Ser Gly Ser Gly Thr Asp Phe Thr Leu Thr Ile Asp Pro
 65                  70                  75                  80

Val Gln Ala Asp Asp Ile Ala Ala Tyr Tyr Cys Gln Gln Ser Arg Glu
                 85                  90                  95

Ser Pro Leu Thr Phe Gly Gly Gly Thr Lys Val Glu Ile Lys
                100                 105                 110

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Phe Thr Phe Ser Ser Ser Ala
  1               5

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Ser Gly Ser Asp Ser Ser Thr
  1               5

<210> SEQ ID NO 47
<211> LENGTH: 20
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 47

Cys Ala Lys Lys Gly Ala Tyr Cys Ser Gly Thr Ile Cys Tyr Asp Pro
1               5                   10                  15

Phe Asp Tyr Trp
            20

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ser Val Ser Ile Ser Ser Ile Asn
1               5

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Ser
1

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Cys Gln Gln Ser Arg Glu Ser Pro Leu Thr Phe
1               5                   10

<210> SEQ ID NO 51
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
gaggtgcagc tggtggagtc tggcggcggc ctggtgcagc caggcggctc tctgagactg      60
tcttgtgccg cttctggctt taccttctcc tcttacgcca tgtcttgggt gcggcaagcc     120
cccggcaagg gcctggagtg ggtgtctgct atctccggcg gcggcgacta tacctactat     180
gccgacagcg tgaagggcag attcaccatc agcagggaca ttccaagaa  cacccctgtac    240 ctgcagatga actccctgag agctgaggat acagccgtgt actattgcgc caaggaggag     300
tgggagctga gaggcccatt tcggtattgg ggccagggca cactggtgac agtctcgagt     360

<210> SEQ ID NO 52
```

<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 52

```
gacatccaga tgacccagag cccttccacc ctgagcgcca gcgtcggaga tagagtgaca    60
attacttgcc gtgccagcca gtccatttcc tcttggctgg cctggtacca gcagaagcct   120
ggcaaggccc ctaagttcct gatctataaa gcttcttccc tggagtctgg agtcccatcc   180
aggttctccg gctctggatc cggaaccgag tttaccctga caatcagctc tctgcagccc   240
gacgattttg ccacatacta ttgtcagcag tataacgggt ttagttggac cttcgggcag   300
ggcacaaaag tggagatcaa a                                             321
```

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Asp Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Glu Trp Glu Leu Arg Gly Pro Phe Arg Tyr Trp Gly Gln
            100                 105                 110

Gly Thr Leu Val Thr Val Ser Ser
        115                 120
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Phe Leu Ile
        35                  40                  45

Tyr Lys Ala Ser Ser Leu Glu Ser Gly Val Pro Ser Arg Phe Ser Gly
    50                  55                  60
```

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Gly Phe Ser Trp
                85                  90                  95

Thr Phe Gly Gln Gly Thr Lys Val Glu Ile Lys
            100                 105

<210> SEQ ID NO 55
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Thr Phe Ser Ser Tyr Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Ser Gly Gly Gly Asp Tyr Thr
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Ala Lys Glu Glu Trp Glu Leu Arg Gly Pro Phe Arg Tyr Trp
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Ser Ile Ser Ser Trp
1               5

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Ala Ser
1

```
<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Gln Gln Tyr Asn Gly Phe Ser Trp Thr Phe
1               5                   10

<210> SEQ ID NO 61
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 63
<211> LENGTH: 894
<212> TYPE: PRT
<213> ORGANISM: Homo sapiens

<400> SEQUENCE: 63

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

```
Gln Ala Gln Gly Pro Pro Glu Pro Val Asp Leu Leu Trp Leu Gln Asp
                165                 170                 175
Ala Val Pro Leu Ala Thr Ala Pro Gly His Gly Pro Gln Arg Ser Leu
            180                 185                 190
His Val Pro Gly Leu Asn Lys Thr Ser Ser Phe Ser Cys Glu Ala His
        195                 200                 205
Asn Ala Lys Gly Val Thr Thr Ser Arg Thr Ala Thr Ile Thr Val Leu
    210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                245                 250                 255
His Cys Thr Leu Gln Ala Val Leu Ser Asp Asp Gly Met Gly Ile Gln
            260                 265                 270
Ala Gly Glu Pro Asp Pro Pro Glu Glu Pro Leu Thr Ser Gln Ala Ser
        275                 280                 285
Val Pro Pro His Gln Leu Arg Leu Gly Ser Leu His Pro His Thr Pro
    290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
        355                 360                 365
Leu Ala Tyr Gln Gly Gln Asp Thr Pro Glu Val Leu Met Asp Ile Gly
    370                 375                 380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                405                 410                 415
Trp Ser Leu Pro Val Pro Leu Glu Ala Trp Arg Pro Gly Gln Ala Gln
            420                 425                 430
Pro Val His Gln Leu Val Lys Glu Pro Ser Thr Pro Ala Phe Ser Trp
        435                 440                 445
Pro Trp Trp Tyr Val Leu Leu Gly Ala Val Val Ala Ala Ala Cys Val
    450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                485                 490                 495
Arg Tyr Arg Val Arg Lys Ser Tyr Ser Arg Arg Thr Thr Glu Ala Thr
            500                 505                 510
Leu Asn Ser Leu Gly Ile Ser Glu Glu Leu Lys Glu Lys Leu Arg Asp
        515                 520                 525
Val Met Val Asp Arg His Lys Val Ala Leu Gly Lys Thr Leu Gly Glu
    530                 535                 540
Gly Glu Phe Gly Ala Val Met Glu Gly Gln Leu Asn Gln Asp Asp Ser
545                 550                 555                 560
Ile Leu Lys Val Ala Val Lys Thr Met Lys Ile Ala Ile Cys Thr Arg
                565                 570                 575
Ser Glu Leu Glu Asp Phe Leu Ser Glu Ala Val Cys Met Lys Glu Phe
```

```
                    580                 585                 590
Asp His Pro Asn Val Met Arg Leu Ile Gly Val Cys Phe Gln Gly Ser
            595                 600                 605

Glu Arg Glu Ser Phe Pro Ala Pro Val Val Ile Leu Pro Phe Met Lys
        610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
    690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
    770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
    850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly Gly Gly Gly Ser Gly Gly Gly Gly Ser Gly Gly Gly Gly Ser
1               5                   10                  15

<210> SEQ ID NO 65
<211> LENGTH: 15
<212> TYPE: PRT
<213> ORGANISM: Artificial Sequence
<220> FEATURE:
```

```
-continued

<223> OTHER INFORMATION: Description of Artificial Sequence: Synthetic
      peptide

<400> SEQUENCE: 65

Cys Ala Ser Arg Glu Tyr Ser Ser Arg Trp His Phe Asp Tyr Trp
1               5                   10                  15

<210> SEQ ID NO 66
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Asp
                20                  25                  30

Thr Ala Val Tyr Tyr
                35

<210> SEQ ID NO 67
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asn Tyr Asn Pro Ser Leu Lys Ser Arg Val Thr Ile Ser Val Asp Thr
1               5                   10                  15

Ser Lys Asn Gln Phe Ser Leu Lys Leu Ser Ser Val Thr Ala Ala Gly
                20                  25                  30

Thr Ala Val Tyr Tyr
                35
```